United States Patent
Okumura et al.

(10) Patent No.: US 9,211,350 B2
(45) Date of Patent: Dec. 15, 2015

(54) COMPOUND WITH AMYLOID AFFINITY

(75) Inventors: Yuki Okumura, Sodegaura (JP);
Yoshifumi Maya, Sodegaura (JP);
Yoshinari Shoyama, Sodegaura (JP);
Takako Onishi, Sodegaura (JP)

(73) Assignee: NIHON MEDI-PHYSICS CO., LTD., Tokyo (JP)

( * ) Notice: Subject to any disclaimer, the term of this patent is extended or adjusted under 35 U.S.C. 154(b) by 0 days.

(21) Appl. No.: 14/128,903

(22) PCT Filed: May 29, 2012

(86) PCT No.: PCT/JP2012/063726
§ 371 (c)(1),
(2), (4) Date: Dec. 23, 2013

(87) PCT Pub. No.: WO2012/176587
PCT Pub. Date: Dec. 27, 2012

(65) Prior Publication Data
US 2014/0121377 A1    May 1, 2014

(30) Foreign Application Priority Data

Jun. 24, 2011  (JP) .................. 2011-140069

(51) Int. Cl.
*C07D 471/04*  (2006.01)
*A61K 51/04*   (2006.01)

(52) U.S. Cl.
CPC .......... *A61K 51/0455* (2013.01); *C07D 471/04* (2013.01)

(58) Field of Classification Search
CPC ........................ C07D 471/04; A61K 51/0455
USPC .......................................... 546/121; 514/300
See application file for complete search history.

(56) References Cited

U.S. PATENT DOCUMENTS 8,303,935 B2  11/2012  Tanifuji et al.
8,399,672 B2   3/2013  Tanifuji et al.
(Continued)

FOREIGN PATENT DOCUMENTS

EP  1956013 A1  8/2008
EP  2019103 A1  1/2009
(Continued)

OTHER PUBLICATIONS

Cai; J. Med. Chem. 2007, 50, 4746-4758.*
(Continued)

*Primary Examiner* — Janet L Andres
*Assistant Examiner* — Daniel Carcanague
(74) *Attorney, Agent, or Firm* — Fitch, Even, Tabin & Flannery LLP

(57) ABSTRACT

A compound represented by the following formula (1), or a salt thereof:

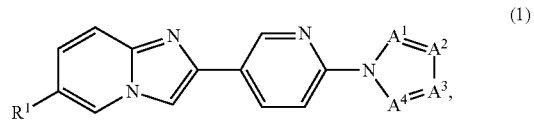

wherein $R^1$ is a radioactive halogen substituent, 0 to 2 of $A^1$, $A^2$, $A^3$ and $A^4$ represent N, and the rest represent —(CH)— is effective as a diagnostic imaging probe targeting amyloid. A diagnostic agent for Alzheimer's disease contains a compound represented by the above formula (1) or a salt thereof. After administration to a patient, the compound and the diagnostic agent for Alzheimer's disease transfer into the patient's brain, and indicate good accumulation on amyloid deposited in the brain.

7 Claims, 5 Drawing Sheets

(56) References Cited

U.S. PATENT DOCUMENTS

| | | |
|---|---|---|
| 2008/0219922 A1 | 9/2008 | Goodman et al. |
| 2009/0162283 A1* | 6/2009 | Bando et al. .................. 424/1.89 |
| 2009/0252679 A1 | 10/2009 | Tanifuji et al. |
| 2010/0069640 A1 | 3/2010 | Tanifuji et al. |
| 2010/0092385 A1 | 4/2010 | Vallin et al. |
| 2010/0092387 A1 | 4/2010 | Tanifuji et al. |
| 2010/0249408 A1 | 9/2010 | Tanifuji et al. |
| 2010/0249418 A1 | 9/2010 | Tanifuji et al. |
| 2010/0249419 A1 | 9/2010 | Tanifuji et al. |
| 2010/0267952 A1 | 10/2010 | Tanifuji et al. |
| 2010/0292479 A1 | 11/2010 | Tanifuji et al. |
| 2012/0070374 A1 | 3/2012 | Gjermund et al. |
| 2012/0263646 A1 | 10/2012 | Catoen et al. |
| 2014/0228569 A1* | 8/2014 | Okumura et al. .................. 546/4 |

FOREIGN PATENT DOCUMENTS

| | | |
|---|---|---|
| EP | 2213671 A1 | 8/2010 |
| EP | 2213672 A1 | 8/2010 |
| EP | 2216050 A1 | 8/2010 |
| EP | 2216051 A1 | 8/2010 |
| EP | 2218463 A1 | 8/2010 |
| JP | 2002-523383 T | 7/2002 |
| JP | 2004-506723 T | 3/2004 |
| JP | 2005-504055 A | 2/2005 |
| JP | 2005-512945 T | 5/2005 |
| WO | 2007033080 A2 | 3/2007 |
| WO | 2007/063946 A1 | 6/2007 |
| WO | 2007/135890 A1 | 11/2007 |
| WO | 2007148755 A1 | 12/2007 |
| WO | 2008065785 A1 | 6/2008 |
| WO | 2008091195 A1 | 7/2008 |
| WO | 2009/054496 A1 | 4/2009 |
| WO | 2009/054497 A1 | 4/2009 |
| WO | 2009/057575 A1 | 5/2009 |
| WO | 2009/057576 A1 | 5/2009 |
| WO | 2009/057578 A1 | 5/2009 |
| WO | WO 2009155024 * | 12/2009 |
| WO | 2010092111 A1 | 8/2010 |
| WO | 2010/128595 A1 | 11/2010 |
| WO | 2011045415 A1 | 4/2011 |

OTHER PUBLICATIONS

WO 2010128595, English language translation from Google Patents, Nov. 11, 2010.*

International Search Report dated Jun. 26, 2012, issued in International Application PCT/JP2012/063726.

Agdeppa et al., "2-Dialkylamino-6-Acylmalononitrile Substituted Naphthalenes (DDNP Analogs): Novel Diagnostic and Therapeutic Tools in Alzheimer's Disease", Molecular Imaging and Biology, vol. 5, No. 6, 2003, pp. 404-417.

Furumoto et al., "[11c]bf-227: A New C-Labeled 2-Ethenylbenzoxazole Derivative for Amyloid-B Plaques Imaging", Radiochemistry: European Journal of Nuclear Medicine and Molecular Imaging, vol. 32, Sup. 1, 2005, PET, P759.

Hardy et al., "Alzheimer's Disease: The Amyloid Cascade Hypothesis", Perspective, Science, vol. 256, Apr. 10, 1992, pp. 184-185.

Klunk et al., "Imaging Brain Amyloid in Alzheimer's Disease with Pittsburgh Compound-B", Annals of Neurology, vol. 55, No. 3, Mar. 2004, pp. 306-319.

Kung et al., "Novel Stilbenes as Probes for Amyloid Plaques", J. Am. Chem. Society, vol. 123, No. 50, 2001, pp. 12740-12741.

McKhann et al., "Clinical diagnosis of Alzheimer's disease: Report of the NINCDS-ADRDA Work Group* under the auspices of Department of Heath and Human Services Task Force on Alzheimer's Disease", Neurology, vol. 34, Jul. 1984, pp. 939-944.

Ono et al., "C-labeled stilbene derivatives as AB-aggregate-specific PET imaging agents for Alzheimer's disease", Elsevier, Nuclear Medicine and Biology, vol. 30, 2003, pp. 565-571.

Verhoeff et al., "In-Vivo Imaging of Alzheimer Disease B-Amyloid With [11C]SB-13 PET", Am. J. Geriatr Psychiatry, 12:6, Nov.-Dec. 2004, pp. 584-595.

Zhuang et al., "Radioiodinated Styrylbenzenes and Thioflavins as Probes for Amyloid Aggregates", J. Med. Chem., vol. 44, 2001, pp. 1905-1914.

Zhuang et al., "IBOX(2-(4'-dimethylaminophenyl)-6-iodobenzoxazole): a ligand for imaging amyloid plaques in the brain", Elsevier, Nuclear Medicine and Biology, vol. 28, 2001, pp. 887-894.

Zhuang et al., "Structure-Activity Relationship of Imidazo[1,2-a]pyridines as Ligands for Detecting B-Amyloid Plaques in the Brain", J. Med. Chem., vol. 46, 2003, pp. 237-243.

Newberg et al., "Safety, Biodistribution, and Dosimetry of 123I-IMPY: A Novel Amyloid Plaque-Imaging Agent for the Diagnosis of Alzheimer's Disease", The Journal of Nuclear Medicine, vol. 47, No. 5, May 2006, pp. 748-754.

Arai et al., "[11C]-BF-227 and PET to Visualize Amyloid in Alzheimer's Disease Patents", Alzheimer's & Dementia: The Journal of the Alzheimer's Association, 2006, 2, Sup. 1, p. S312.

Clark et al., "Imaging Amyloid With 1123 IMPY SPECT", Alzheimer's & Dementia: The Journal of the Alzheimer's Association, 2006, 2, Sup. 1, p. S342.

International Preliminary Report on Patentability (English Translation).

Extended European Search Report issued against PCT/JP2012/063726 on Jan. 28, 2015.

Office Action dated Feb. 4, 2015 issued by Chinese Patent Office against the corresponding CN application 2012800275450.

International Preliminary Report on Patentability (English Translation), Dated Mar. 6, 2014.

Chinese Office Action issued against corresponding Chinese Application No. 201280027545.0 on Sep. 23, 2015.

* cited by examiner

COMPOUND WITH AMYLOID AFFINITY

CROSS-REFERENCE TO RELATED APPLICATIONS

This Application is a U.S. National Stage Application filed under 35 U.S.C. §371 of International Application PCT/JP2012/063726, filed May 29, 2012, designating the United States, which claims priority from Japanese Patent Application 2011-140069, filed June 24, 2011, the complete disclosures of which are hereby incorporated herein by reference in their entirety for all purposes.

TECHNICAL FIELD

The present invention relates to a compound for use in diagnosis of cerebral degenerative disease. More specifically, the invention relates to a compound useful for amyloid detection at lesion sites in diagnosis of Alzheimer's disease and other diseases with amyloid accumulation.

BACKGROUND ART

Diseases with the onset of deposition of a fibrous protein called amyloid in various organs or tissues in bodies are generally referred to as amyloidosis. A feature common to amyloidosis is that the fibrous protein called amyloid which is enriched with the β-sheet structure is deposited at various organs systemically or at sites topically so that functional abnormalities are triggered in the organs or tissues.

Alzheimer's disease (hereinafter referred to as AD), which is a typical amyloidosis disease, is known as a disease causing dementia. This disease is lethal with progressive deposition of amyloid in brain, and thus is said to be a disease that causes concern in society compared with other amyloidosis diseases. In recent years, the number of AD patients is rapidly increasing in developed countries with aging societies, thereby causing a social problem.

From the pathohistological viewpoint, AD is characterized by three pathological findings in brain, namely development of senile plaques, formation of neurofibrillary tangles, and extensive neuronal loss. The senile plaque has a structure mainly composed of amyloid, and is said to appear at the earliest stage of AD onset and thus is pathologically found in brain 10 or more years before appearance of clinical symptoms.

AD is diagnosed by carrying out various evaluations of cognitive functions (for example, Hasegawa scale, ADAS-JCog and MMSE) in auxiliary combination with imaging diagnosis such as CT and MRI. However, the method based on such evaluations of cognitive functions is low in diagnostic sensitivity at the early stage of the onset, and is furthermore problematic in that diagnostic results are susceptible to inborn cognitive functions of individuals. At present, it is practically impossible to establish a definite diagnosis of AD while an AD patient is still alive, because the definite diagnosis requires a biopsy of a lesion (Non-Patent Document 1).

Meanwhile, a report tells that amyloid constituting senile plaques is an aggregate of amyloid β protein (hereinafter referred to as Aβ). Also, numerous reports tell that the Aβ aggregate forms a β-sheet structure that causes nerve cell toxicity. Based on these findings, the so-called "Amyloid Cascade Hypothesis" is proposed, which suggests that cerebral deposition of Aβ triggers the downstream phenomena, namely, formation of neurofibrillary tangles and neuronal loss (Non-Patent Document 2).

Based on these facts, attempts have recently been made to detect AD in vivo using a compound having high affinity with amyloid as a marker.

Many of such probes for imaging diagnoses of cerebral amyloid are hydrophobic low-molecular weight compounds that are high in affinity with amyloid and high in cerebral transferability and are labeled with various radioactive species such as $^{11}C$, $^{18}F$ and $^{123}I$. For example, reports tell $^{11}C$ or radioactive halogen labeled forms of compounds including various thioflavin derivatives such as 6-iodo-2-[4'-(N,N-dimethylamino)phenyl]benzothiazole (hereinafter referred to as TZDM) and 6-hydroxy-2-[4'-(N-methylamino)phenyl]benzothiazole (hereinafter referred to as 6-0H-BTA-1) (Patent Document 1, Non-Patent Document 3); stilbene compounds such as (E)-4-methylamino-4'-hydroxystilbene (hereinafter referred to as SB-13) and (E)-4-dimethylamino-4'-iodostilbene (hereinafter referred to as m-I-SB) (Patent Document 2, Non-Patent Document 4, Non-Patent Document 5); benzoxazole derivatives such as 6-iodo-2-[4'-(N,N-dimethylamino)phenyl]benzoxazole (hereinafter referred to as IBOX) and 6-[2-(fluoro)ethoxy]-2-[2-(2-dimethylaminothiazol-5-yl)ethenyl]benzoxazole (Non-Patent Document 6, Non-Patent Document 7), DDNP derivatives such as 2-(1-(6-[(2-fluoroethyl)(methyl)amino]-2-naphthyl)ethylidene)malononitrile (hereinafter referred to as FDDNP) (Patent Document 4, Non-Patent Document 8); and imidazopyridine derivatives such as 6-iodo-2-[4'-(N,N-dimethylamino)phenyl]imidazo[1,2-a]pyridine (hereinafter referred to as IMPY) (Patent Document 3, Non-Patent Document 9), and radioactive halogen labeled forms of compounds including compounds in which a nitrogen-containing 5-membered aromatic heterocyclic group is attached to an imidazopyridine-phenyl via carbons (Patent Document 5 and Patent Document 6). Further, some of these probes for imaging diagnosis have been studied on human imaging and have been reported to show a significant accumulation of radioactivity in AD patient's brain compared with normal persons (Non-Patent Document 10, Non-Patent Document 11, Non-Patent Document 12, Non-Patent Document 13).

CONVENTIONAL TECHNICAL DOCUMENTS

Patent Documents

[Patent Document 1] JP-T-2004-506723
[Patent Document 2] JP-T-2005-504055
[Patent Document 3] JP-T-2005-512945
[Patent Document 4] JP-T-2002-523383
[Patent Document 5] International Publication No. WO2007/063946 pamphlet
[Patent Document 6] International Publication No. WO2010/128595 pamphlet

Non-Patent Documents

[Non-Patent Document 1] J. A. Hardy & G. A. Higgins, "Alzheimer's Disease: The Amyloid Cascade Hypothesis.", Science, 1992, 256, p. 184-185
[Non-Patent Document 2] G. McKhann et al., "Clinical diagnosis of Alzheimer's disease: Report of the NINCDS-ADRDA Work Group under the auspices of Department of Health and Human Services Task Force on Alzheimer's Disease.", Neurology, 1984, 34, p. 939-944
[Non-Patent Document 3] Z.-P. Zhuang et al., "Radioiodinated Styrylbenzenes and Thioflavins as Probes for Amyloid Aggregates.", J. Med. Chem., 2001, 44, p. 1905-1914

[Non-Patent Document 4] Masahiro Ono et al., "11C-labeled stilbene derivatives as Aβ-aggregate-specific PET imaging agents for Alzheimer's disease.", Nuclear Medicine and Biology, 2003, 30, p. 565-571

[Non-Patent Document 5] H. F. Kung et al., "Novel Stilbenes as Probes for amyloid plaques.", J. American Chemical Society, 2001, 123, p. 12740-12741

[Non-Patent Document 6] Zhi-Ping Zhuang et al., "IBOX(2-(4'-dimethylaminophenyl)-6-iodobensoxazole): a ligand for imaging amyloid plaques in the brain.", Nuclear Medicine and Biology, 2001, 28, p. 887-894

[Non-Patent Document 7] Furumoto Y et al., "[11C]BF-227: A New 11C-Labeled 2-Ethenylbenzoxazole Derivative for Amyloid-β Plaques Imaging.", European Journal of Nuclear Medicine and Molecular Imaging, 2005, 32, Sup. 1, P759

[Non-Patent Document 8] Eric D. Agdeppa et al., "2-Dialkylamino-6-Acylmalononitrile Substituted Naphthalenes (DDNP Analogs): Novel Diagnostic and Therapeutic Tools in Alzheimer's Disease.", Molecular Imaging and Biology, 2003, 5, p. 404-417

[Non-Patent Document 9] Zhi-Ping Zhuang et al., "Structure-Activity Relationship of Imidazo[1,2-a]pyridines as Ligands for Detecting β-Amyloid Plaques in the Brain.", J. Med. Chem., 2003, 46, p. 237-243

[Non-Patent Document 10] W. E. Klunk et al., "Imaging brain amyloid in Alzheimer's disease with Pittsburgh Compound-B.", Ann. Neurol., 2004, 55, p. 306-319

[Non-Patent Document 11] Nicolaas P. L. G. Verhoeff et al., "In-Vivo Imaging of Alzheimer Disease β-Amyloid With [11C]SB-13 PET.", American Journal of Geriatric Psychiatry, 2004, 12, p. 584-595

[Non-Patent Document 12] Hiroyuki Arai et al., "[11C]-BF-227 AND PET to Visualize Amyloid in Alzheimer's Disease Patients", Alzheimer's & Dementia: The Journal of the Alzheimer's Association, 2006, 2, Sup. 1, S312

[Non-Patent Document 13] Christopher M. Clark et al., "Imaging Amyloid with 1123 IMPY SPECT", Alzheimer's & Dementia: The Journal of the Alzheimer's Association, 2006, 2, Sup. 1, 5342

DISCLOSURE OF THE INVENTION

Problems to be Solved by the Invention

As described above, various compounds are disclosed as probes for imaging diagnosis for amyloid, and researched for clinical application. However, there has been no compound which is confirmed to have a clinically tolerable property. In addition, considering a broad range of clinical application, a compound having a sufficient diagnosing property in case of being labeled not only by PET isotope, but also SPECT isotope is desired.

The present invention has been made under the above-mentioned circumstances, and aims at providing a compound that is effective as a probe targeting amyloid for imaging diagnosis and a diagnostic agent for Alzheimer's disease comprising the compound.

Means for Solving the Problems

As a result of repeated studies, the inventors have found that a diagnostic agent for Alzheimer's disease with a sufficient diagnostic property can be obtained by using a compound in which a 5-membered nitrogen-containing heterocycle is attached to a carbon at 2'-position of the pyridinyl group of an imidazopyridine-pyridinyl skeleton via a nitrogen atom of the nitrogen-containing heterocycle, and thus have completed the present invention.

According to one aspect of the present invention, a compound represented by the following formula (1):

or a salt thereof, and a diagnostic agent for Alzheimer's disease comprising a compound represented by the above formula (1) or a salt thereof are provided.

In the formula (1), $R^1$ is a radioactive halogen substituent. As $R^1$, can be used various radioactive halogens, preferably a radioactive halogen selected from the group consisting of $^{18}F$, $^{76}Br$, $^{123}I$, $^{124}I$, $^{125}I$ and $^{131}I$, and more preferably $^{18}F$ or $^{123}I$.

Zero to 2 of $A^1$, $A^2$, $A^3$ and $A^4$ represent N, and the rest thereof represent CH, and preferably, 1 or 2 thereof represent N and the rest thereof represent CH.

Therefore, according to the preferable embodiment of the present invention, a compound represented by the following formula (3) to (9):

or a salt thereof, and a diagnostic agent for Alzheimer's disease comprising a compound represented by the above formula (3) to (9) or a salt thereof are provided.

According to another aspect of the present invention, a compound represented by the following formula (2):

(2)

or a salt thereof is provided.

In the formula (2), $R^2$ is a group selected from the group consisting of a non-radioactive halogen substituent, nitro group, trialkylammonium group having alkyl chains with 1 to 4 carbon atoms, trialkylstannyl substituent having alkyl chains with 1 to 4 carbon atoms and triphenylstannyl group. 0 to 2 of $A^5$, $A^6$, $A^7$ and $A^8$ represent N and the rest thereof represent CH.

The compound represented by the formula (2) can be suitably used as a labeling precursor for the compound of the above mentioned formula (1).

As a non-radioactive halogen substituent, a halogen capable of being a target of nucleophilic substitution reactions using a radioactive fluorine or a halogen capable of being a target of isotope exchange reactions with a radioactive iodine can be used, and preferably chlorine, iodine or bromine can be used. As a trialkylstannyl substituent, various substituents can be used, and trimethylstannyl substituent and tributylstannyl substituent are preferably used.

Therefore, according to a preferable embodiment of the present invention, a compound represented by the following formula (10) to (16) is provided:

(10)

(11)

(12)

(13)

(14)

(15)

(16)

Effects of the Invention

According to the present invention, a novel compound having affinity with amyloid and a diagnostic agent for Alzheimer's disease have become available, which have an excellent capability of imaging amyloid in living bodies.

BEST MODE FOR CARRYING OUT THE INVENTION

A Method for Synthesis of a Precursor Compound for a Radioactive Halogen-Labeled Compound Hereinafter, a method for synthesis of a precursor compound for a radioactive halogen-labeled compound according to an embodiment of the present invention is described, taking the case of 2-[2-(1H-1,2,3-triazole-1-yl)pyridine-5-yl]-6-tributylstannylimidazo[1,2-a]pyridine as an example. The present compound is a compound which is suitably used as a precursor compound for a radioactive iodine-labeled compound according to the present invention.

Meanwhile, the synthetic method described hereinafter is just an illustration of a preferred synthetic method, and does not intend to limit the production method of the compound according to the present invention.

Figure 1:
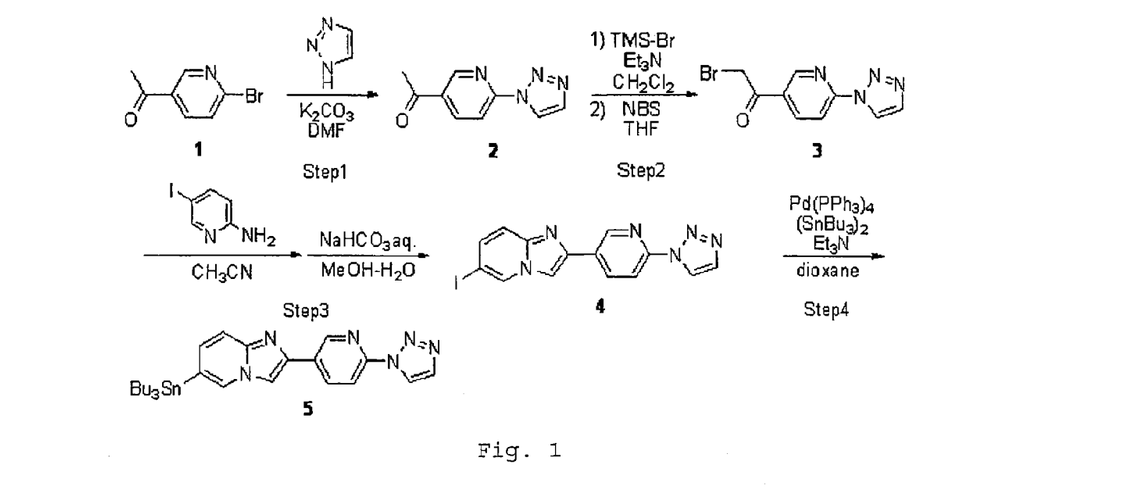
FIG. 1 is a scheme of synthesis of 2-[2-(1H-1,2,3-triazole-1-yl)pyridine-5-yl]-6-tributylstannylimidazo[1,2-a]pyridine.

FIG. 1 shows a scheme of synthesis of 2-[2-(1H-1,2,3-triazole-1-yl)pyridine-5-yl]-6-tributylstannylimidazo[1,2-a]pyridine. For the synthesis of 2-[2-(1H-1,2,3-triazole-1-yl)pyridine-5-yl]-6-tributylstannylimidazo[1,2-a]pyridine, 1H-1,2,3-triazole is first allowed to react with 5-acetyl-2-bromopyridine to prepare 5-acetyl-2-(1H-1,2,3-triazole-1- yl)pyridine (FIG. 1, step 1). This step can be conducted in accordance with, for example, the following procedures.

First, 5-acetyl-2-bromopyridine and 1H-1,2,3,-triazole are dissolved in dimethylformamide, and potassium carbonate is added thereto. This mixture is stirred at 100° C. for 2-6 hours, and then the reaction solution is poured into water and extracted with dichloromethane. The dichloromethane layer is concentrated and purified by chromatography, to obtain 5-acetyl-2-(1H-1,2,3-triazole-1-yl)pyridine (FIG. 1, step 1). The amount of potassium carbonate to be used may be an amount that can neutralize hydrobromic acid generated during reaction, and is typically an amount equivalent or more to 5-acetyl-2-bromopyridine as the raw material. In addition, the amount of 1H-1,2,3-triazol to be used may be an amount excessive relative to the substrate, and is typically about 3.0 times greater in molar ratio than 5-acetyl-2-bromopyridine.

Next, the obtained 5-acetyl-2-(1H-1,2,3-triazole-1-yl)pyridine is dissolved in dichloromethane and triethylamine. The resulting solution is cooled down to about 0° C., and then bromotrimethylsilane is added thereto. This reaction solution is stirred at room temperature for 10-24 hours. Then, the reaction solution is poured into water and extracted with dichloromethane, and the dichloromethane layer is concentrated. The oily substance resulting from concentration is dried sufficiently and dissolved in tetrahydrofuran. This mixture is cooled down to about 0° C., N-bromosuccinimide is added thereto and stirred at room temperature for about 10-60 minutes. After the completion of the reaction, the solvent is distilled off and purified by chromatography, to obtain 5-(2-bromoacetyl)-2-(1H-1,2,3-triazole-1-yl)pyridine (FIG. 1, step 2). The amount of bromotrimethylsilane may be an amount equivalent or more relative to the reaction substrate, and is typically about 2.0 times greater in molar ratio than 5-acetyl-2-(1H-1,2,3-triazole-1-yl)pyridine. In addition, the amount of triethylamine may be an amount that can neutralize hydrobromic acid generated during reaction, and is typically an amount excessive relative to trimethylsilane bromide. The amount of N-bromosuccinimide may be an amount equivalent or more relative to the reaction substrate, and is preferably about 1.0 time in molar ratio as much as 5-acetyl-2-(1H-1,2,3-triazole-1-yl)pyridine.

The obtained 5-(2-bromoacetyl)-2-(1H-1,2,3-triazole-1-yl)pyridine is allowed to react with 2-amino-5-iodopyridine in accordance with known methods (for example, the method described in a literature, Zhi-Ping Zhuang et al., J. Med. Chem., 2003, 46, p. 237-243), to obtain 6-iodo-2-[2-(1H-1,2,3-triazole-1-yl)pyridine-5-yl]imidazo[1,2-a]pyridine (FIG. 1, step 3).

Then, the obtained 6-iodo-2-[2-(1H-1,2,3-triazole-1-yl)pyridine-5-yl]imidazo[1,2-a]pyridine is allowed to react with bis(tributyltin) (FIG. 1, step 4) in accordance with known methods (for example, the method described in a literature, Zhi-Ping Zhuang et al., J. Med. Chem., 2003, 46, p. 237-243), and purified, to obtain 2-[2-(1H-1,2,3-triazole-1-yl)pyridine-5-yl]-6-tributylstannylimidazo[1,2-a]pyridine as the target compound.

When a compound with a substituent at 6-position of the imidazopyridine ring being a trialkylstannyl substituent other than the tributylstannyl substituent is obtained, various bis(trialkyltin)s that fit purposes can be used instead of bis(tributyltin) in step 4 of FIG. 1. For example, when a compound having a trimethylstannyl substituent as a substituent at the 6-position is synthesized, a reaction similar to the above may be performed using bis(trimethyltin) in step 4 of FIG. 1. In addition, a compound with a substituent at 6-position of the imidazopyridine ring being a nitro group can be obtained by performing the reaction in accordance with known methods, except that 2-amino-5-nitropyridine is used instead of 2-amino-5-iodopyridine in step 3 of FIG. 1, and step 4 is omitted.

In addition, other precursor compounds according to the present invention can be synthesized by using generally-available raw materials and combining reactions known to the skilled in the art. For example, a compound in which $A^5$ is N and all $A^6$, $A^7$ and $A^8$ are CH in the above formula (2) can be synthesized in accordance with the above steps of FIG. 1, except that pyrazole is used instead of 1H-1,2,3,-triazole in step 1 of FIG. 1. In addition, a compound in which all $A^5$, $A^6$, $A^7$ and $A^8$ are CH in the above formula (2) can be synthesized in accordance with the above steps of FIG. 1, except that pyrrole is used instead of 1H-1,2,3,-triazole in FIG. 1, step 1.

(A Method for Synthesis of a Radioactive Halogen-Labeled Compound)

Next, a method for production of a radioactive halogen-labeled compound according to another aspect of the present invention will be described, taking the case of radioactive iodine-labeled compounds as examples.

The synthesis of radioactive iodine-labeled compounds can be performed by dissolving, in an inert organic solvent, the labeling precursor compound prepared in a manner as described above, adding thereto a [$^{123}$I]sodium iodide solution or the like obtained by known methods, and adding thereto an acid and an oxidizing agent so as to allow a reaction to proceed. As the inert organic solvent in which the labeling precursor compound is dissolved, various solvents having no reactivity with the labeling precursor and [$^{123}$I]sodium iodide or the like can be used, and preferably acetonitrile can be used.

As the acid, various acids can be used, and preferably hydrochloric acid can be used.

The oxidizing agent is not particularly limited as long as it can effect the oxidation of iodine in the reaction solution, and is preferably hydrogen peroxide or peracetic acid. The amount of the oxidizing agent to be added may be an amount sufficient to oxidize iodine in the reaction solution.

A compound labeled with a radioactive halogen other than iodine can be synthesized by labeling a labeling precursor that fits a purpose of synthesis with a radioactive halogen that fits the purpose. For example, in order to synthesize [$^{18}$F]-6-fluoro-2-[2-(1H-1,2,3-triazole-1-yl)pyridine-5-yl]imidazo[1,2-a]pyridine, the labeling precursor 6-nitro-2-[2-(1H-1,2,3-triazole-1-yl)pyridine-5-yl]imidazo[1,2-a]pyridine can be reacted with [$^{18}$F]fluoride ion in the presence of a phase transfer catalyst and potassium carbonate.

(Methods for Preparing and Using a Diagnostic Agent in Accordance with the Present Invention)

The diagnostic agent according to the present invention can be prepared as a solution which comprises the present radioactive halogen-labeled compound blended in water, a physiological saline solution or a Ringer's solution optionally adjusted to an appropriate pH, like other commonly-known radioactive diagnostic agents. In this instance, concentration of the present compound should be adjusted to not more than the concentration at which stability of the present compound is ensured. Dosage of the present compound is not specifically limited as long as it is sufficient to obtain an image of distribution of an administered agent. For example, when $^{123}$I-labeled compounds or $^{18}$F-labeled compounds are used, about 50 to 600 MBq per adult body of 60 kg weight can be administered intravenously or locally. Distribution of administered agents can be imaged by known methods. For example, $^{123}$I-labeled compounds can be imaged by a SPECT apparatus while $^{18}$F-labeled compounds can be imaged by a PET apparatus.

EXAMPLE

Hereinafter, the present invention is explained below in more detail by describing Examples, Comparative Examples and Reference Examples. However, these Examples never limit the scope of the present invention.

In the following Examples, the names of the individual compounds used in the experiment are defined as shown in Table 1.

TABLE 1

Names of the compounds used for evaluation in Examples

| Compound name | Common name |
|---|---|
| Compound 1 | [$^{123}$I]-6-iodo-2-[2-(1H-1,2,3-triazole-1-yl)pyridine-5-yl]imidazo[1,2-a]pyridine |
| Compound 2 | [$^{123}$I]-6-iodo-2-[2-(2H-1,2,3-triazole-2-yl)pyridine-5-yl]imidazo[1,2-a]pyridine |
| Compound 3 | [$^{123}$I]-6-iodo-2-[2-(1H-imidazole-1-yl)pyridine-5-yl]imidazo[1,2-a]pyridine |
| Compound 4 | [$^{123}$I]-6-iodo-2-[2-(1H-1,2,4-triazole-1-yl)pyridine-5-yl]imidazo[1,2-a]pyridine |
| Compound 5 | [$^{123}$I]-6-iodo-2-[2-(pyrazole-1-yl)pyridine-5-yl]imidazo[1,2-a]pyridine |

Example 1

Synthesis of 2-[2-(1H-1,2,3,-triazole-1-yl)pyridine-5-yl]-6-tributylstannylimidazo[1,2-a]pyridine 207 mg (corresponding to 3.00 mmol) of 1H-1,2,3-triazole was dissolved in 5 mL of dimethylformamide. Then, 200 mg (corresponding to 1.00 mmol) of 5-acetyl-2-bromopyridine and 414 mg (corresponding to 3.00 mmol) of potassium carbonate were added thereto. The resulting solution was heated at 100° C. for 3 hours. After the completion of the reaction, the reaction solution was cooled down to room temperature, supplemented with a saturated ammonium chloride aqueous solution and water, and extracted 3 times with dichloromethane. The combined dichloromethane layer was washed with water and a saturated saline solution, dried over anhydrous magnesium sulfate, and then concentrated under reduced pressure. The resulting crude product was purified by silica gel column chromatography (elution solvent: dichloromethane/ethyl acetate=4/1), to obtain 57.2 mg (corresponding to 0.304 mmol) of 5-acetyl-2-(1H-1,2,3-triazole-1-yl)pyridine (FIG. 1, step 1).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 9.05 (d, J=2.3 Hz, 1H), 8.65 (d, J=1.1 Hz, 1H), 8.46 (dd, J=8.7, 2.3 Hz, 1H), 8.34 (d, J=8.7 Hz, 1H), 7.86 (d, J=1.1 Hz, 1H), 2.68 (s, 3H).

57.2 mg (corresponding to 0.304 mmol) of 5-acetyl-2-(1H-1,2,3-triazole-1-yl)pyridine was dissolved in 2.0 mL of dichloromethane and 127 µL of triethylamine, and then 78.9 µL (corresponding to 0.608 mmol) of bromotrimethylsilane was dropped under ice cooling. The resulting solution was stirred over night at room temperature under argon gas atmosphere, and then the reaction solution was supplemented with water and extracted 3 times with dichloromethane. The combined dichloromethane layer was washed with water and a saturated saline solution, and dried over magnesium sulfate. The solvent was distilled off, the resulting residue was dissolved in 2.0 mL of tetrahydrofuran, and 54.1 mg (corresponding to 0.304 mmol) of N-bromosuccinimide was added thereto under ice cooling. The resulting solution was stirred at room temperature for 30 minutes. After the completion of the reaction, the solvent was distilled off under reduced pressure, and the residue was purified by flash silica gel column chromatography (elution solvent: dichloromethane/ethyl acetate=4/1), to obtain 66.4 mg (corresponding to 0.249 mmol) of 5-(2-bromoacetyl)-2-(1H-1,2,3-triazole-1-yl)pyridine (FIG. 1, step 2).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 9.12 (d, J=2.1 Hz, 1H), 8.67 (d, J=1.1 Hz, 1H), 8.51 (dd, J=8.7, 2.3 Hz, 1H), 8.38 (d, J=8.7 Hz, 1H), 7.87 (d, J=1.1 Hz, 1H), 4.44 (s, 2H).

66.4 mg (corresponding to 0.249 mmol) of 5-(2-bromoacetyl)-2-(1H-1,2,3-triazole-1-yl)pyridine and 54.8 mg (corresponding to 0.249 mmol) of 2-amino-5-iodopyridine were dissolved in 2.0 mL of acetonitrile. The resulting solution was heated under reflux for 1.5 hours in an oil bath at 100° C. After the completion of the reaction, the reaction solution was cooled down to room temperature, and precipitates were filtered. The precipitates were washed with acetonitrile and dried under reduced pressure. The resulting crude crystals were suspended in a mixed solution of 2 mL of water and 2 mL of methanol. Then, about 1 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 44.0 mg (corresponding to 0.113 mmol) of 6-iodo-2-[2-(1H-1,2,3-triazole-1-yl)pyridine-5-yl]imidazo[1,2-a]pyridine (FIG. 1, step 3).

NMR apparatus employed: JNM-ECP-500 (manufactured by Japan Electron Optics Laboratory Co., Ltd. (JEOL))

$^1$H-NMR (solvent: dimethylsulfoxide-d6; resonance frequency: 500 MHz): δ 9.11 (d, J=2.3 Hz, 1H), 8.91 (brs, 1H), 8.82 (d, J=0.9 Hz, 1H), 8.57 (dd, J=8.5, 2.3 Hz, 1H), 8.47 (s, 1H), 8.16 (d, J=8.5 Hz, 1H), 7.94 (d, J=0.9 Hz, 1H), 7.45 (brs, 2H).

20 mg (corresponding to 0.0515 mmol) of 6-iodo-2-[2-(1H-1,2,3-triazole-1-yl)pyridine-5-yl]imidazo[1,2-a]pyridine was dissolved in 0.8 mL of dioxane, and 0.2 mL of triethylamine was added thereto. Then, 51.5 µL (corresponding to 0.130 mmol) of bis(tributyltin) and 6.0 mg (a catalytic amount) of tetrakis-triphenylphosphine palladium were added thereto. After the reaction mixture was stirred at 100° C. for 16 hours, the solvent was distilled off under reduced pressure. The residue was purified by flash silica gel column chromatography (elution solvent: hexane/ethyl acetate=2/1). The resulting crude crystals were recrystallized from hexane-ethyl acetate, to obtain 8.7 mg (corresponding to 0.016 mmol) of 2-[2-(1H-1,2,3-triazole-1-yl)pyridine-5-yl]-6-tributylstannylimidazo[1,2-a]pyridine (FIG. 1, step 4).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 9.05 (d, J=1.4 Hz, 1H), 8.63 (brs, 1H), 8.48 (dd, J=8.4, 2.1 Hz, 1H), 8.28 (d, J=8.4 Hz, 1H), 8.03 (t, J=14.7 Hz, 1H), 7.94 (s, 1H), 7.85 (d, J=1.4 Hz, 1H), 7.63 (d, J=8.7 Hz, 1H), 7.23 (d, J=8.7 Hz, 1H), 1.64-1.49 (m, 6H), 1.36 (tt, J=7.3, 7.3 Hz, 6H), 1.21-1.07 (m, 6H), 0.91 (t, J=7.3 Hz, 9H).

Example 2

Synthesis of [$^{123}$I]-6-iodo-2-[2-(1H-1,2,3-triazole-1-yl)pyridine-5-yl]imidazo[1,2-a]pyridine
(Compound 1)

To 90 µL of a solution (concentration: 1 mg/mL) in acetonitrile of 2-[2-(1H-1,2,3-triazole-1-yl)pyridine-5-yl]-6-tributylstannylimidazo[1,2-a]pyridine synthesized in Example 1, 85 μL of 2 mol/L hydrochloric acid, 60 μL of [$^{123}$I]sodium iodide of 641 MBq and 10 μL of 30% (w/v) hydrogen peroxide were added. After the mixed solution was left to stand at 40° C. for 10 minutes, it was subjected to HPLC under the following conditions, to obtain a fraction of [$^{123}$I]-6-iodo-2-[2-(1H-1,2,3-triazole-1-yl)pyridine-5-yl]imidazo[1,2-a]pyridine.

HPLC Conditions:
Column: YMC PackPro C8 (trade name; manufactured by YMC; size: 4.6×150 mm)
Mobile phase: 0.1% trifluoroacetic acid-containing water/0.1% trifluoroacetic acid-containing acetonitrile=80/20 to 0/100 (20 minutes)
Flow rate: 1.0 mL/min.
Detector: Ultraviolet visible absorptiometer (Detection wavelength: 260 nm) and radioactivity counter (manufactured by raytest: type STEFFI)

5 mL of water was added to the fraction. The resulting solution was passed through Sep-Pak (registered trademark) C18 column (trade name: Sep-Pak (registered trademark) Light C18 Cartridges manufactured by Waters; the packed amount of the packing agent: 130 mg) so that the column adsorbed and collected [$^{123}$I]-6-iodo-2-[2-(1H-1,2,3-triazole-1-yl)pyridine-5-yl]imidazo[1,2-a]pyridine. The column was rinsed with 1 mL of water, and then 1 mL of diethyl ether was passed therethrough, to elute [$^{123}$I]-6-iodo-2-[2-(1H-1,2,3-triazole-1-yl)pyridine-5-yl]imidazo[1,2-a]pyridine. The obtained radioactivity was 239 MBq at the end of synthesis. Further, TLC analysis was conducted under the following conditions, and as a result, the radiochemical purity of the compound was 99.1%.

TLC Analysis Conditions:
TLC plate: Silica Gel 60 $F_{254}$ (trade name; manufactured by Merck & Co., Inc.)
Mobile phase: Ethyl acetate/methanol/diethylamine=100/4/1
Detector: Rita Star (trade name; manufactured by raytest)

Example 3

Figure 2:
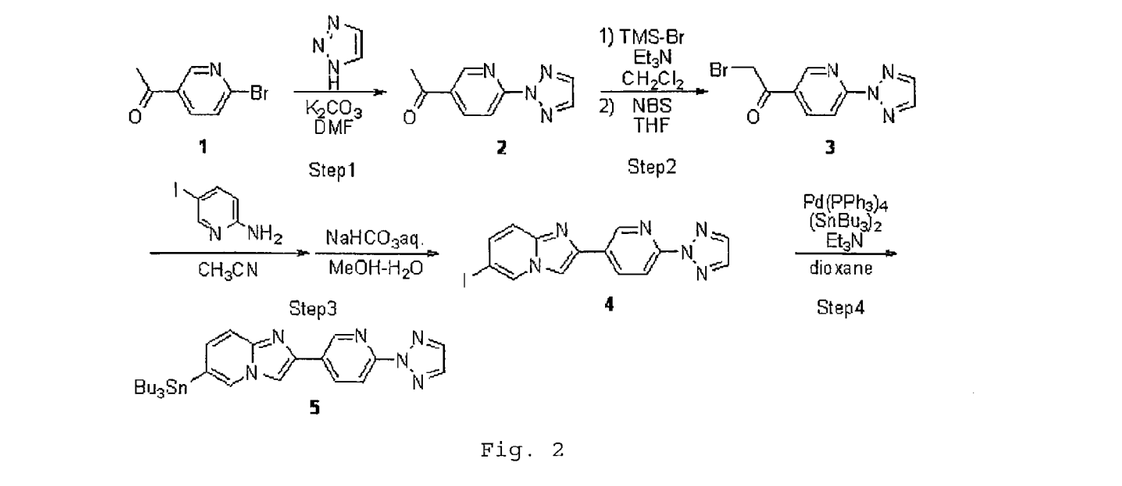
FIG. 2 is a scheme of synthesis of 2-[2-(2H-1,2,3-triazole-2-yl)pyridine-5-yl]-6-tributylstannylimidazo[1,2-a]pyridine.

Synthesis of 2-[2-(2H-1,2,3-triazole-2-yl)pyridine-5-yl]-6-tributylstannylimidazo[1,2-a]pyridine 207 mg (corresponding to 3.00 mmol) of 1H-1,2,3-triazole was dissolved in 5 mL of dimethylformamide. Then, 200 mg (corresponding to 1.00 mmol) of 5-acetyl-2-bromopyridine and 414 mg (corresponding to 3.00 mmol) of potassium carbonate were added thereto. The resulting solution was heated at 100° C. for 3 hours. After the completion of the reaction, the reaction solution was cooled down to room temperature, supplemented with a saturated ammonium chloride aqueous solution and water, and extracted 3 times with dichloromethane. The combined dichloromethane layer was washed with water and a saturated saline solution, dried over anhydrous magnesium sulfate, and then concentrated under reduced pressure. The resulting crude product was purified by silica gel column chromatography (elution solvent: dichloromethane/ethyl acetate=4/1), to obtain 31.9 mg (corresponding to 0.170 mmol) of 5-acetyl-2-(2H-1,2,3-triazole-2-yl)pyridine (FIG. 2, step 1).

NMR apparatus employed: JNM-ECP-500 (manufactured by Japan Electron Optics Laboratory Co., Ltd. (JEOL))
$^1$H-NMR (solvent: chlorofolm-d1; resonance frequency: 500 MHz): δ 9.13 (d, J=2.3 Hz, 1H), 8.45 (dd, J=8.6, 2.3 Hz, 1H), 8.21 (d, J=8.6 Hz, 1H), 7.97 (s, 2H), 2.69 (s, 3H).

31.9 mg (corresponding to 0.170 mmol) of 5-acetyl-2-(2H-1,2,3-triazole-2-yl)pyridine was dissolved in 1.0 mL of dichloromethane and 71 μL of triethylamine, and then 44.1 μL (corresponding to 0.51 mmol) of bromotrimethylsilane was dropped under ice cooling. The resulting solution was stirred over night at room temperature under argon gas atmosphere, and then, the reaction solution was supplemented with water and extracted 3 times with dichloromethane. The combined dichloromethane layer was washed with water and a saturated saline solution, and dried over anhydrous magnesium sulfate. The solvent was distilled off, the resulting residue was dissolved in 1.0 mL of tetrahydrofuran, and 33.3 mg (corresponding to 0.17 mmol) of N-bromosuccinimide was added thereto under ice cooling. The resulting solution was stirred at room temperature for 30 minutes. After the completion of the reaction, the solvent was distilled off under reduced pressure, and the residue was purified by flash silica gel column chromatography (elution solvent: dichloromethane/ethyl acetate=2/1), to obtain 20.2 mg (corresponding to 0.076 mmol) of 5-(2-bromoacetyl)-2-(2H-1,2,3-triazole-2-yl)pyridine (FIG. 2, step 2).

NMR apparatus employed: JNM-ECP-500 (manufactured by Japan Electron Optics Laboratory Co., Ltd. (JEOL))
$^1$H-NMR (solvent: chlorofolm-d1; resonance frequency: 500 MHz): δ 9.18 (d, J=2.1 Hz, 1H), 8.49 (dd, J=8.5, 2.1 Hz, 1H), 8.24 (d, J=8.5 Hz, 1H), 7.98 (s, 2H), 4.45 (s, 2H).

20.4 mg (corresponding to 0.0764 mmol) of 5-(2-bromoacetyl)-2-(2H-1,2,3-triazole-2-yl)pyridine and 16.8 mg (corresponding to 0.0764 mmol) of 2-amino-5-iodopyridine were dissolved in 2.0 mL of acetonitrile. The resulting solution was heated under reflux for 1.5 hours in an oil bath at 100° C. After the completion of the reaction, the reaction solution was cooled down to room temperature, and precipitates were filtered. The precipitates were washed with acetonitrile and dried under reduced pressure. The resulting crude crystals were suspended in a mixed solution of 2 mL of water and 2 mL of methanol. Then, about 1 mL of a saturated sodium hydrogencarbonate solution was added thereto, and the mixture was sonicated for 10 minutes using an ultrasonic washing machine. Precipitates were filtered and recovered from the resulting mixture, sufficiently washed with water, and dried under reduced pressure, to obtain 10.4 mg (corresponding to 0.027 mmol) of 6-iodo-2-[2-(2H-1,2,3-triazole-2-yl)pyridine-5-yl]imidazo[1,2-a]pyridine (FIG. 2, step 3).

NMR apparatus employed: JNM-ECP-500 (manufactured by Japan Electron Optics Laboratory Co., Ltd. (JEOL))
$^1$H-NMR (solvent: dimethylsulfoxide-d6; resonance frequency: 500 MHz): δ 9.13 (d, J=2.3 Hz, 1H), 8.96 (brs, 1H), 8.56 (dd, J=8.7, 2.3 Hz, 1H), 8.50 (s, 1H), 8.17 (s, 2H), 8.10 (d, J=8.7 Hz, 1H), 7.48 (brs, 2H).

7 mg (corresponding to 0.018 mmol) of 6-iodo-2-[2-(2H-1,2,3-triazole-2-yl)pyridine-5-yl]imidazo[1,2-a]pyridine was dissolved in 0.5 mL of dioxane, and 0.1 mL of triethylamine was added thereto. Then, 18 μL (corresponding to 0.036 mmol) of bis(tributyltin) and 2 mg (a catalytic amount) of tetrakis-triphenylphosphine palladium were added thereto. After the reaction mixture was stirred at 100° C. for 16 hours, the solvent was distilled off under reduced pressure. The residue was purified by flash silica gel column chromatography (elution solvent: hexane/ethyl acetate=2/1). The resulting crude crystals were recrystallized from hexane-ethyl acetate, to obtain 2.3 mg (corresponding to 0.004 mmol) of 2-[2-(2H-1,2,3-triazole-2-yl)pyridine-5-yl]-6-tributylstannylimidazo[1,2-a]pyridine (FIG. 2, step 4).

NMR apparatus employed: JNM-ECP-500 (manufactured by Japan Electron Optics Laboratory Co., Ltd. (JEOL))
$^1$H-NMR (solvent: chlorofolm-d1; resonance frequency: 500 MHz): δ 9.09 (d, J=2.1 Hz, 1H), 8.52 (dd, J=8.6, 2.1 Hz, 1H), 8.16 (d, J=8.6 HZ, 1H), 8.03 (s, 1H), 7.97 (s, 1H), 7.91

(s, 2H), 7.632 (d, J=8.9 Hz, 1H), 7.2 (d, J=8.9 Hz, 1H), 1.60-1.50 (m, 6H), 1.36 (tt, J=7.3, 7.3 Hz, 6H), 1.20-1.06 (m, 6H), 0.91 (t, J=7.1 HZ, 9H).

Example 4

Synthesis of [$^{123}$I]-6-iodo-2-[2-(2H-1,2,3-triazole-2-yl)pyridine-5-yl]imidazo[1,2-a]pyridine
(Compound 2)

To 45 μL of a solution (concentration: 1 mg/mL) in acetonitrile of 2-[2-(2H-1,2,3-triazole-2-yl)pyridine-5-yl]-6-tributylstannylimidazo[1,2-a]pyridine synthesized in Example 3, 42.5 μL of 2 mol/L hydrochloric acid, 30 μL of [$^{123}$I]sodium iodide of 341 MBq and 5 μL of 30% (w/v) hydrogen peroxide were added. After the mixed solution was left to stand at 40° C. for 10 minutes, it was subjected to HPLC under the following conditions, to obtain a fraction of [$^{123}$I]-6-iodo-2-[2-(2H-1,2,3-triazole-2-yl)pyridine-5-yl]imidazo[1,2-a]pyridine.
HPLC Conditions:
Column: YMC PackPro C8 (trade name; manufactured by YMC; size: 4.6×150 mm)
Mobile phase: 0.1% trifluoroacetic acid-containing water/0.1% trifluoroacetic acid-containing acetonitrile=80/20 to 0/100 (20 minutes)
Flow rate: 1.0 mL/min.
Detector: Ultraviolet visible absorptiometer (Detection wavelength: 260 nm) and radioactivity counter (manufactured by raytest: type STEFFI)

5 mL of water was added to the fraction. The resulting solution was passed through Sep-Pak (registered trademark) C18 column (trade name: Sep-Pak (registered trademark) Light C18 Cartridges manufactured by Waters; the packed amount of the packing agent: 130 mg) so that the column adsorbed and collected [$^{123}$I]-6-iodo-2-[2-(2H-1,2,3-triazole-2-yl)pyridine-5-yl]imidazo[1,2-a]pyridine. The column was rinsed with 1 mL of water, and then 1 mL of diethyl ether was passed therethrough, to elute [$^{123}$I]-6-iodo-2-[2-(2H-1,2,3-triazole-2-yl)pyridine-5-yl]imidazo[1,2-a]pyridine. The obtained radioactivity was 91.8 MBq at the end of synthesis. Further, TLC analysis was conducted under the following conditions, and as a result, the radiochemical purity of the compound was 97.6%.
TLC Analysis Conditions:
TLC plate: Silica Gel 60 F$_{254}$ (trade name; manufactured by Merck & Co., Inc.)
Mobile phase: Ethyl acetate/methanol/diethylamine=100/4/1
Detector: Rita Star (trade name; manufactured by raytest)

Example 5

Figure 3:
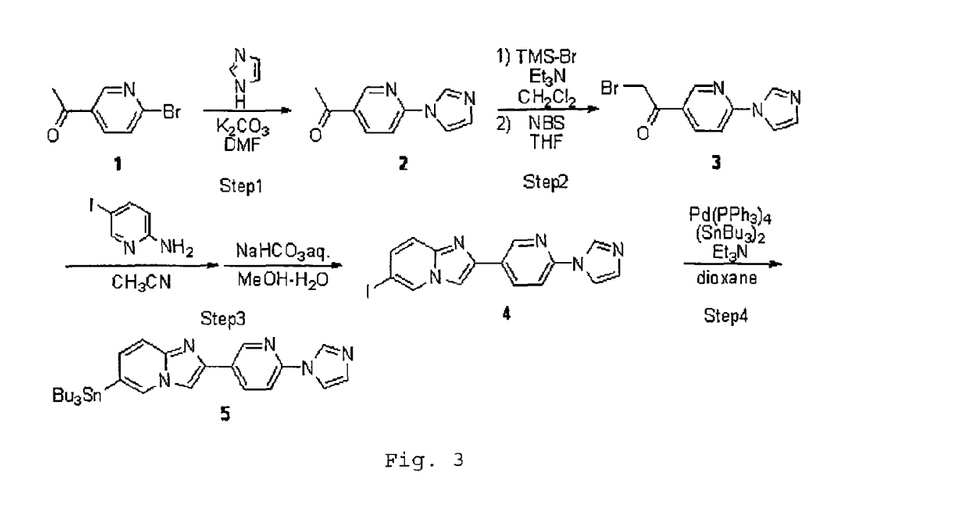
FIG. 3 is a scheme of synthesis of 2-[2-(1H-imidazole-1-yl)pyridine-5-yl]-6-tributylstannylimidazo[1,2-a]pyridine.

Synthesis of 2-[2-(1H-imidazole-1-yl)pyridine-5-yl]-6-tributylstannylimidazo[1,2-a]pyridine 204 mg (corresponding to 3.00 mmol) of imidazole was dissolved in 5 mL of dimethylformamide. Then, 200 mg (corresponding to 1.00 mmol) of 5-acetyl-2-bromopyridine and 414 mg (corresponding to 3.00 mmol) of potassium carbonate were added thereto. The resulting solution was heated at 100° C. for 3 hours. After the completion of the reaction, the reaction solution was cooled down to room temperature, supplemented with a saturated ammonium chloride aqueous solution and water, and extracted 3 times with dichloromethane. The combined dichloromethane layer was washed with water and a saturated saline solution, dried over anhydrous magnesium sulfate, and then concentrated under reduced pressure. The resulting crude product was purified by silica gel column chromatography (elution solvent: dichloromethane/ethyl acetate=4/1), to obtain 87 mg (corresponding to 0.462 mmol) of 5-acetyl-2-(1H-imidazole-1-yl)pyridine (FIG. 3, step 1).
NMR apparatus employed: JNM-ECP-500 (manufactured by Japan Electron Optics Laboratory Co., Ltd. (JEOL))
$^1$H-NMR (solvent: chlorofolm-d1; resonance frequency: 500 MHz): δ 9.03 (d, J=2.3 Hz, 1H), 8.43 (brs, 1H), 8.38 (dd, J=8.5, 2.3 Hz, 1H), 7.69 (brs, 1H), 7.44 (d, J=8.5 Hz, 1H), 7.23 (brs, 1H), 2.66 (s, 3H).

87 mg (corresponding to 0.462 mmol) of 5-acetyl-2-(1H-imidazole-1-yl)pyridine was dissolved in 3.0 mL of dichloromethane and 193 μL of triethylamine, and then 120 μL (corresponding to 0.924 mmol) of bromotrimethylsilane was dropped under ice cooling. The resulting solution was stirred over night at room temperature under argon gas atmosphere, and then the reaction solution was supplemented with water and extracted 3 times with dichloromethane. The combined dichloromethane layer was washed with water and a saturated saline solution, and dried over magnesium sulfate. The solvent was distilled off, the resulting residue was dissolved in 3.0 mL of tetrahydrofuran, and 82.2 mg (corresponding to 0.462 mmol) of N-bromosuccinimide was added thereto under ice cooling. The resulting solution was stirred at room temperature for 30 minutes. After the completion of the reaction, the solvent was distilled off under reduced pressure, and the residue was purified by flash silica gel column chromatography (elution solvent: dichloromethane/ethyl acetate=2/1), to obtain 24.3 mg (corresponding to 0.091 mmol) of 5-(2-bromoacetyl)-2-(1H-imidazole-1-yl)pyridine (FIG. 3, step 2).

24.3 mg (corresponding to 0.0876 mmol) of 5-(2-bromoacetyl)-2-(1H-imidazole-1-yl)pyridine and 19.3 mg (corresponding to 0.0876 mmol) of 2-amino-5-iodopyridine were dissolved in 2.0 mL of acetonitrile. The resulting solution was heated under reflux for 1.5 hours in an oil bath at 100° C. After the completion of the reaction, the reaction solution was cooled down to room temperature, and precipitates were filtered. The precipitates were washed with acetonitrile and dried under reduced pressure. The resulting crude crystals were suspended in a mixed solution of 2 mL of water and 2 mL of methanol. Then, about 1 mL of a saturated sodium hydrogencarbonate solution was added thereto, and the mixture was sonicated for 10 minutes using an ultrasonic washing machine. Precipitates were filtered and recovered from the resulting mixture, sufficiently washed with water, and dried under reduced pressure, to obtain crude crystals of 6-iodo-2-[2-(1H-imidazole-1-yl)pyridine-5-yl]imidazo[1,2-a]pyridine. The resulting crude crystals were purified by flash silica gel column chromatography (elution solvent: ethyl acetate/methanol=10/1), to obtain 17.7 mg (corresponding to 0.046 mmol) of 6-iodo-2-[2-(1H-imidazole-1-yl)pyridine-5-yl]imidazo[1,2-a]pyridine (FIG. 3, step 3).
NMR apparatus employed: JNM-ECP-500 (manufactured by Japan Electron Optics Laboratory Co., Ltd. (JEOL))
$^1$H-NMR (solvent: dimethylsulfoxide-d6; resonance frequency: 500 MHz): δ 9.05 (d, J=2.3 Hz, 1H), 8.94 (s, 1H), 8.55 (s, 1H), 8.48 (dd, J=8.5, 2.3 Hz, 1H), 8.46 (s, 1H), 7.97 (s, 1H), 7.89 (d, J=8.5 Hz, 1H), 7.47 (brs, 2H), 7.14 (s, 1H).

10 mg (corresponding to 0.029 mmol) of 6-iodo-2-[2-(1H-imidazole-1-yl)pyridine-5-yl]imidazo[1,2-a]pyridine was dissolved in 0.5 mL of dioxane, and 0.1 mL of triethylamine was added thereto. Then, 26 μL (corresponding to 0.052 mmol) of bis(tributyltin) and 3 mg (a catalytic amount) of tetrakis-triphenylphosphine palladium were added thereto. After the reaction mixture was stirred at 100° C. for 16 hours, the solvent was distilled off under reduced pressure. The residue was purified by flash silica gel column chromatography (elution solvent: hexane/ethyl acetate=2/1). The resulting crude crystals were recrystallized from hexane-ethyl acetate, to obtain 3.1 mg (corresponding to 0.006 mmol) of 2-[2-(1H-imidazole-1-yl)pyridine-5-yl]-6-tributylstannylimidazo[1,2-a]pyridine (FIG. 3, step 4).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 8.99 (d, J=2.3 Hz, 1H), 8.44 (dd, J=8.5, 2.3 Hz, 1H), 8.40 (brs, 1H), 8.02 (brs, 1H), 7.91 (s, 1H), 7.68 (brs, 1H), 7.62 (d, J=8.5 Hz, 1H), 7.44 (d, J=7.8 Hz, 1H), 7.23 (brs, 1H), 7.22 (d, J=7.8 Hz, 1H), 1.62-1.50 (m, 6H), 1.36 (tt, J=7.3, 7.3 Hz, 6H), 1.20-1.08 (m, 6H), 0.91 (t, J=7.3 Hz, 9H).

Example 6

Synthesis of [$^{123}$I]-6-iodo-2-[2-(1H-imidazole-1-yl)pyridine-5-yl]imidazo[1,2-a]pyridine (Compound 3)

To 45 μL of a solution (concentration: 1 mg/mL) in acetonitrile of 2-[2-(1H-imidazole-1-yl)pyridine-5-yl]-6-tributylstannylimidazo[1,2-a]pyridine synthesized in Example 5, 42.5 μL of 2 mol/L hydrochloric acid, 30 μL of [$^{123}$I]sodium iodide of 485 MBq and 5 μL of 30% (w/v) hydrogen peroxide were added. After the mixed solution was left to stand at 40° C. for 10 minutes, it was subjected to HPLC under the following conditions, to obtain a fraction of [$^{123}$I]-6-iodo-2-[2-(1H-imidazole-1-yl)pyridine-5-yl]imidazo[1,2-a]pyridine.
HPLC Conditions:
Column: YMC PackPro C8 (trade name; manufactured by YMC; size: 4.6×150 mm)
Mobile phase: 0.1% trifluoroacetic acid-containing water/0.1% trifluoroacetic acid-containing acetonitrile=90/10 to 0/100 (25 minutes)
Flow rate: 1.0 mL/min.
Detector: Ultraviolet visible absorptiometer (Detection wavelength: 260 nm) and radioactivity counter (manufactured by raytest: type STEFFI)

5 mL of water was added to the fraction. The resulting solution was passed through Sep-Pak (registered trademark) C18 column (trade name: Sep-Pak (registered trademark) Light C18 Cartridges manufactured by Waters; the packed amount of the packing agent: 130 mg) so that the column adsorbed and collected [$^{123}$I]-6-iodo-2-[2-(1H-imidazole-1-yl)pyridine-5-yl]imidazo[1,2-a]pyridine. The column was rinsed with 1 mL of water, and then 1 mL of diethyl ether was passed therethrough, to elute [$^{123}$I]-6-iodo-2-[2-(1H-imidazole-1-yl)pyridine-5-yl]imidazo[1,2-a]pyridine. The obtained radioactivity was 40.1 MBq at the end of synthesis. Further, TLC analysis was conducted under the following conditions, and as a result, the radiochemical purity of the compound was 91.3%.
TLC Analysis Conditions:
TLC plate: Silica Gel 60 F$_{254}$ (trade name; manufactured by Merck & Co., Inc.)
Mobile phase: Ethyl acetate/methanol/diethylamine=100/4/1
Detector: Rita Star (trade name; manufactured by raytest)

Example 7

Figure 4:
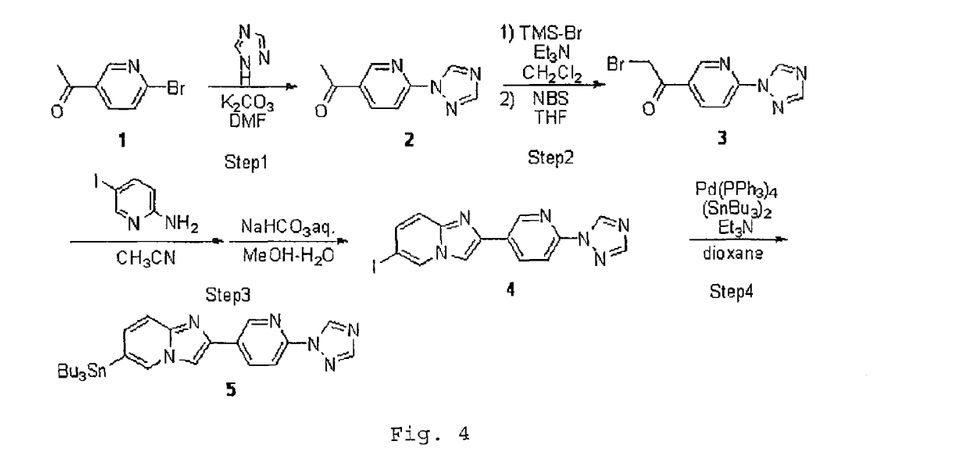
FIG. 4 is a scheme of synthesis of 2-[2-(1H-1,2,4,-triazole-1-yl)pyridine-5-yl]-6-tributylstannylimidazo[1,2-a]pyridine.

Synthesis of 2-[2-(1H-1,2,4-triazole-1-yl)pyridine-5-yl]-6-tributylstannylimidazo[1,2-a]pyridine 622 mg (corresponding to 9.00 mmol) of 1H-1,2,4-triazole was dissolved in 10 mL of dimethylformamide. Then, 600 mg (corresponding to 3.00 mmol) of 5-acetyl-2-bromopyridine and 1.24 g (corresponding to 9.00 mmol) of potassium carbonate were added thereto. The resulting solution was heated at 100° C. for 3 hours. After the completion of the reaction, the reaction solution was cooled down to room temperature, supplemented with a saturated ammonium chloride aqueous solution and water, and extracted 3 times with dichloromethane. The combined dichloromethane layer was washed with water and a saturated saline solution, dried over anhydrous magnesium sulfate, and then concentrated under reduced pressure. The resulting crude product was purified by silica gel column chromatography (elution solvent: dichloromethane/ethyl acetate=4/1), to obtain 480 mg (corresponding to 2.55 mmol) of 5-acetyl-2-(1H-1,2,4-triazole-1-yl)pyridine (FIG. 4, step 1).

480 mg (corresponding to 2.55 mmol) of 5-acetyl-2-(1H-1,2,4-triazole-1-yl)pyridine was dissolved in 10 mL of dichloromethane and 1.07 mL of triethylamine, and then 662 μL (corresponding to 5.10 mmol) of bromotrimethylsilane was dropped under ice cooling. The resulting solution was stirred over night at room temperature under argon gas atmosphere, and then supplemented with water and extracted 3 times with dichloromethane. The combined dichloromethane layer was washed with water and a saturated saline solution, and dried over magnesium sulfate. The solvent was distilled off, the resulting residue was dissolved in 10 mL of tetrahydrofuran, and 454 mg (corresponding to 2.55 mmol) of N-bromosuccinimide was added thereto under ice cooling. The resulting solution was stirred at room temperature for 30 minutes. After the completion of the reaction, the solvent was distilled off under reduced pressure, and the residue was purified by flash silica gel column chromatography (elution solvent: dichloromethane/ethyl acetate=2/1), to obtain 657 mg (corresponding to 2.46 mmol) of 5-(2-bromoacetyl)-2-(1H-1,2,4-triazole-1-yl)pyridine (FIG. 4, step 2).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 9.27 (brs, 1H), 9.07 (d, J=2.1 Hz, 1H), 8.48 (dd, J=8.5, 2.3 Hz, 1H), 8.15 (s, 1H), 8.06 (d, J=8.5 Hz, 1H), 4.43 (s, 2H).

657 mg (corresponding to 2.46 mmol) of 5-(2-bromoacetyl)-2-(1H-1,2,4-triazole-1-yl)pyridine and 541 mg (corresponding to 2.46 mmol) of 2-amino-5-iodopyridine were dissolved in 5.0 mL of acetonitrile. The resulting solution was heated under reflux for 1.5 hours in an oil bath at 100° C. After the completion of the reaction, the reaction solution was cooled down to room temperature, and precipitates were filtered. The precipitates were washed with acetonitrile and dried under reduced pressure. The resulting crude crystals were suspended in a mixed solution of 2 mL of water and 2 mL of methanol. Then, about 1 mL of a saturated sodium hydrogencarbonate solution was added thereto, and the mixture was sonicated for 10 minutes using an ultrasonic washing machine. Precipitates were filtered and recovered from the resulting mixture, sufficiently washed with water, and dried under reduced pressure, to obtain 675 mg (corresponding to 1.74 mmol) of 6-iodo-2-[2-(1H-1,2,4-triazole-1-yl)pyridine-5-yl]imidazo[1,2-a]pyridine (FIG. 4, step 3).

NMR apparatus employed: JNM-ECP-500 (manufactured by Japan Electron Optics Laboratory Co., Ltd. (JEOL))

$^1$H-NMR (solvent: dimethylsulfoxide-d1; resonance frequency: 500 MHz): δ 9.38 (brs, 1H), 9.10 (d, J=2.1 Hz, 1H), 8.96 (brs, 1H), 8.57 (dd, J=8.5, 2.1 Hz, 1H), 8.49 (s, 1H), 8.31 (s, 1H), 7.96 (d, J=8.5 Hz, 1H), 7.49 (brs, 2H).

100 mg (corresponding to 0.258 mmol) of 6-iodo-2-[2-(1H-1,2,4-triazole-1-yl)pyridine-5-yl]imidazo[1,2-a]pyridine was dissolved in 5.0 mL of dioxane, and 0.5 mL of triethylamine was added thereto. Then, 258 µL (corresponding to 0.516 mmol) of bis(tributyltin) and 29.8 mg (a catalytic amount) of tetrakis-triphenylphosphine palladium were added thereto. After the reaction mixture was stirred at 100° C. for 16 hours, the solvent was distilled off under reduced pressure. The residue was purified by flash silica gel column chromatography (elution solvent: hexane/ethyl acetate=2/1). The resulting crude crystals were recrystallized from hexane-ethyl acetate, to obtain 47 mg (corresponding to 0.085 mmol) of 2-[2-(1H-1,2,4-triazole-1-yl)pyridine-5-yl]-6-tributylstannylimidazo[1,2-a]pyridine (FIG. 4, step 4).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 9.21 (s, 1H), 8.99 (d, J=2.1 Hz, 1H), 8.48 (dd, J=8.4, 2.1 Hz, 1H), 8.12 (s, 1H), 7.97 (d, J=8.4 Hz, 1H), 8.02 (t, J=14.7 Hz, 1H), 7.93 (s, 1H), 7.62 (d, J=8.7 Hz, 1H), 7.22 (d, J=8.7 Hz, 1H), 1.65-1.49 (m, 6H), 1.36 (tt, J=7.3, 7.3 Hz, 6H), 1.21-1.07 (m, 6H), 0.91 (t, J=7.3 Hz, 9H).

Example 8

Synthesis of [$^{123}$I]-6-iodo-2-[2-(1H-1,2,4-triazole-1-yl)pyridine-5-yl]imidazo[1,2-a]pyridine (Compound 4)

To 90 µL of a solution (concentration: 1 mg/mL) in acetonitrile of 2-[2-(1H-1,2,4-triazole-1-yl)pyridine-5-yl]-6-tributylstannylimidazo[1,2-a]pyridine synthesized in Example 7, 85 µL of 2 mol/L hydrochloric acid, 60 µL of [$^{123}$I]sodium iodide of 1127 MBq and 10 µL of 30% (w/v) hydrogen peroxide were added. After the mixed solution was left to stand at 40° C. for 10 minutes, it was subjected to HPLC under the following conditions, to obtain a fraction of [$^{123}$I]-6-iodo-2-[2-(1H-1,2,4-triazole-1-yl)pyridine-5-yl]imidazo[1,2-a]pyridine.

HPLC Conditions:
Column: YMC PackPro C8 (trade name; manufactured by YMC; size: 4.6×150 mm)
Mobile phase: 0.1% trifluoroacetic acid-containing water/ 0.1% trifluoroacetic acid-containing acetonitrile=90/10 to 0/100 (20 minutes)
Flow rate: 1.0 mL/min.
Detector: Ultraviolet visible absorptiometer (Detection wavelength: 260 nm) and radioactivity counter (manufactured by raytest: type STEFFI)

5 mL of water was added to the fraction. The resulting solution was passed through Sep-Pak (registered trademark) C18 column (trade name: Sep-Pak (registered trademark) Light C18 Cartridges manufactured by Waters; the packed amount of the packing agent: 130 mg) so that the column adsorbed and collected [$^{123}$I]-6-iodo-2-[2-(1H-1,2,4-triazole-1-yl)pyridine-5-yl]imidazo[1,2-a]pyridine. The column was rinsed with 1 mL of water, and then 1 mL of diethyl ether was passed therethrough, to elute [$^{123}$I]-6-iodo-2-[2-(1H-1,2,4-triazole-1-yl)pyridine-5-yl]imidazo[1,2-a]pyridine. The obtained radioactivity was 536 MBq at the end of synthesis. Further, TLC analysis was conducted under the following conditions, and as a result, the radiochemical purity of the compound was 95.5%.

TLC Analysis Conditions:
TLC plate: Silica Gel 60 $F_{254}$ (trade name; manufactured by Merck & Co., Inc.)
Mobile phase: Ethyl acetate/methanol/diethylamine=100/4/1
Detector: Rita Star (trade name; manufactured by raytest)

Reference Example 1

Synthesis of [$^{123}$I]-IMPY

[$^{123}$I]-IMPY was synthesized in accordance with the following steps for use in Comparative Examples for evaluation on measurement of amyloid binding property and accumulation in brain.

In accordance with the method described in a literature (Zhi-Ping Zhuang et al., J. Med. Chem., 2003, 46, p. 237-243), 2-[4'-(N,N-dimethylamino)phenyl]-6-tributylstannylimidazo[1,2-a]pyridine was synthesized, and dissolved in acetonitrile (concentration: 1 mg/mL). To 50 µL of the resulting solution, 50 µL of 2 mol/L hydrochloric acid, 80 µL of [$^{123}$I]sodium iodide of 1075 MBq, 23 µL of a 1 mmol/L sodium iodide solution and 15 µL of 30% (w/v) hydrogen peroxide were added. After the mixed solution was left to stand at 40° C. for 10 minutes, the solution was subjected to HPLC under the same conditions as in Example 2, to obtain a fraction of [$^{123}$I]-IMPY.

10 ml of water was added to the fraction. The resulting solution was passed through Sep-Pak C18 column (trade name: Sep-Pak (registered trademark) Light C18 Cartridges manufactured by Waters; the packed amount of the packing agent: 130 mg), so that the column adsorbed and collected the [$^{123}$I]-IMPY. The column was rinsed with 1 mL of water, and then 1 mL of diethyl ether was passed therethrough, to elute [$^{123}$I]-IMPY. The obtained radioactivity was 170 MBq at the end of synthesis. Further, TLC analysis was conducted under the same conditions as described in Example 2, and as a result, the radiochemical purity of the compound was 98.5%.

Example 9

Measurement of Partition Coefficient Based on the Octanol Extraction Method

Partition coefficients based on the octanol extraction method (hereinafter referred to as log $P_{octanol}$) were measured, which are generally known as an indicator of permeability of compounds through the blood-brain barrier (hereinafter referred to as BBB).

Method

Compound 1, Compound 2, Compound 3 and Compound 4 were adjusted to about 1 MBq/mL respectively using a water saturated 1-octanol solution to obtain sample solutions. Each sample solution in an amount of 30 µL was added to three microtubes. The three microtubes to which each sample solution was added were supplemented with both water saturated 1-octanol and 1-octanol saturated water so as to make the volume to be 200 µL, 400 µL or 800 µL, respectively (referred to as 200 µL sample, 400 µL sample and 800 µL sample, respectively). Each microtube was subjected to stirring, and then was shaken for 5 minutes (20 to 25±2° C., 20 rpm/min). Next, the mixture in each microtube was centrifuged (23° C., 3000 g×20 min.) with a centrifuge (type: T2-MC, manufactured by BECKMAN), and then 50 µL each of the octanol layer and the water layer was obtained, and subjected to measurement of radioactivity with an Autowell Gamma system (Type: ARC-7001, manufactured by Aloka). Using the obtained count, log $P_{octanol}$ was calculated in accordance with the following equation (1). Meanwhile, the value of log $P_{octanol}$ was an average value of the values which were respectively calculated for the 200 µL sample, the 400 µL sample and the 800 µL sample.

$$\log P_{octanol} = \log_{10}\left(\frac{\text{Radioactivity count of octanol layer}}{\text{Radioactivity count of water layer}}\right) \quad (1)$$

The results are shown in Table 2. log $P_{octanol}$ values of Compound 1, Compound 2, Compound 3 and Compound 4 were 2.10, 2.05, 1.91 and 2.23, respectively. It is known that an optimum log $P_{octanol}$ value of compounds regarding BBB permeability is between 1 and 3 (Douglas D. Dischino et al., J. Nucl. Med., (1983), 24, p. 1030-1038). From the above results, it is implied that Compound 1, Compound 2, Compound 3 and Compound 4 have a BBB permeability.

TABLE 2

| logP$_{octanol}$ value of the present compound | |
|---|---|
| Compound | logP$_{octanol}$ value |
| Compound 1 | 2.10 |
| Compound 2 | 2.05 |
| Compound 3 | 1.91 |
| Compound 4 | 2.23 |

Example 10

Figure 5:
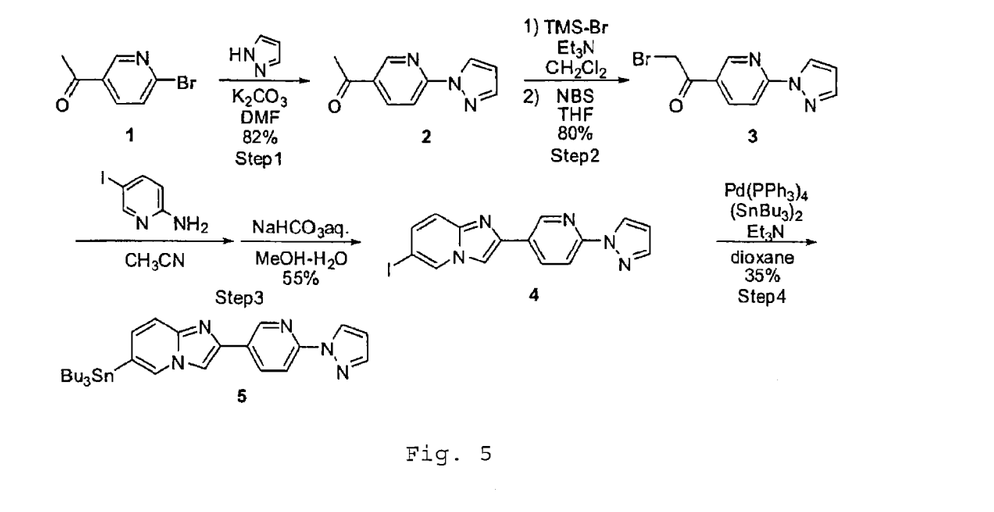
FIG. 5 is a scheme of synthesis of 2-[2-(pyrazole-1-yl)pyridine-5-yl]-6-tributylstannylimidazo[1,2-a]pyridine.

Synthesis of 2-[2-(pyrazole-1-yl)pyridine-5-yl]-6-tributylstannylimidazo[1,2-a]pyridine 407.9 mg (corresponding to 5.99 mmol) of pyrazole was dissolved in 10 mL of dimethylformamide. Then, 400.0 mg (corresponding to 1.99 mmol) of 5-acetyl-2-bromopyridine and 827.9 mg (corresponding to 5.99 mmol) of potassium carbonate were added thereto. The resulting solution was heated at 100° C. for 5 hours. After the completion of the reaction, the reaction solution was cooled down to room temperature, supplemented with water, and extracted twice with dichloromethane. The combined dichloromethane layer was washed with water and a saturated saline solution, dried over anhydrous magnesium sulfate, and then concentrated under reduced pressure. The resulting crude product was purified by silica gel column chromatography (elution solvent: dichloromethane/ethyl acetate=50/1), to obtain 304.0 mg (corresponding to 1.62 mmol) of 5-acetyl-2-(pyrazole-1-yl)pyridine (FIG. 5, step 1).

100.0 mg (corresponding to 0.53 mmol) of 5-acetyl-2-(pyrazole-1-yl)pyridine was dissolved in 4 mL of dichloromethane and 230 µL of triethylamine, and then 140 µL (corresponding to 1.07 mmol) of bromotrimethylsilane was dropped under ice cooling. The resulting solution was stirred over night at room temperature under argon gas atmosphere. Then, the reaction solution was washed with water and a saturated saline solution and dried over magnesium sulfate. The solvent was distilled off, and the resulting residue was dissolved in 4 mL of tetrahydrofuran, 94.3 mg (corresponding to 0.53 mmol) of N-bromosuccinimide was added thereto. The resulting solution was stirred at room temperature for an hour. After the completion of the reaction, the solvent was distilled off under reduced pressure, and the residue was purified by flash silica gel column chromatography (elution solvent: dichloromethane/ethyl acetate=50/1), to obtain 100.0 mg (corresponding to 0.38 mmol) of 5-(2-bromoacetyl)-2-(pyazole-1-yl)pyridine (FIG. 5, step 2).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 9.02 (d, J=1.9 Hz, 1H), 8.63 (d, J=1.9 Hz, 1H), 8.38 (dd, J=8.7, 1.9 Hz, 1H), 8.10 (d, J=8.7 Hz, 1H), 7.79 (s, 1H), 6.52 (t, J=1.9 Hz, 1H), 4.41 (s, 2H).

100.0 mg (corresponding to 0.38 mmol) of 5-(2-bromoacetyl)-2-(pyrazole-1-yl)pyridine and 83.6 mg (corresponding to 0.38 mmol) of 2-amino-5-iodopyridine were dissolved in 3.8 mL of acetonitrile. The resulting solution was heated under reflux for 4 hours in an oil bath at 100° C. After the completion of the reaction, the reaction solution was cooled down to room temperature, and precipitates were filtered. The precipitates were washed with acetonitrile and dried under reduced pressure. The resulting crude crystals were suspended in a mixed solution of 50 mL of water and 50 mL of methanol. Then, about 50 mL of a saturated sodium hydrogencarbonate solution was added thereto, and the mixture was sonicated for an hour using an ultrasonic washing machine. Precipitates were filtered from the resulting mixture, sufficiently washed with water, and dried under reduced pressure, to obtain 80.2 mg (corresponding to 0.21 mmol) of 2-[2-(pyrazole-1-yl)pyridine-5-yl]-6-iodoimidazo[1,2-a]pyridine (FIG. 5, step 3).

NMR apparatus employed: JNM-ECP-500 (manufactured by Japan Electron Optics Laboratory Co., Ltd. (JEOL))

$^1$H-NMR (solvent: dimethylformamide-d6; resonance frequency: 500 MHz): δ 9.04 (d, J=2.3 Hz, 1H), 8.97 (s, 1H), 8.66 (d, J=2.3 Hz, 1H), 8.50 (dd, J=8.3, 2.3 Hz, 1H), 8.46 (s, 1H), 8.01 (d, J=8.3 Hz, 1H), 7.86-7.85 (m, 1H), 7.48 (s, 2H), 6.61-6.60 (m, 1H).

50.0 mg (corresponding to 0.129 mmol) of 2-[2-(pyrazole-1-yl)pyridine-5-yl]-6-iodoimidazo[1,2-a]pyridine was dissolved in 2.0 mL of dioxane, and 0.5 mL of triethylamine was added thereto. Then, 129 µL (corresponding to 0.258 mmol) of bis(tributyltin) and 15.0 mg (a catalytic amount) of tetrakis-triphenylphosphine palladium were added thereto. After the reaction mixture was stirred at 100° C. for 26 hours, the solvent was distilled off under reduced pressure. The residue was purified by flash silica gel column chromatography (elution solvent: hexane/ethyl acetate=2/1). The resulting crude crystals were recrystallized from hexane-ethyl acetate, to obtain 25.1 mg (corresponding to 0.046 mmol) of 2-[2-(pyrazole-1-yl)pyridine-5-yl]-6-tributylstannylimidazo[1,2-a]pyridine (FIG. 5, step 4).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 8.94 (d, J=2.3 Hz, 1H), 8.66 (d, J=2.3 Hz, 1H), 8.40 (dd, J=8.7, 2.3 Hz, 1H), 8.05 (d, J=8.7 Hz, 1H), 8.01 (s, 1H), 7.89 (s, 1H), 7.75 (s, 1H), 7.61 (d, J=8.7 Hz, 1H), 7.20 (d, J=8.7 Hz, 1H), 6.48 (s, 1H), 1.59-1.53 (m, 6H), 1.39-1.32 (m, 6H), 1.14-1.09 (m, 6H), 0.90 (t, J=7.4 Hz, 9H).

Example 11

Synthesis of [$^{123}$I]-6-iodo-2-[2-(pyrazole-1-yl)pyridine-5-yl]imidazo[1,2-a]pyridine (Compound 5)

To 90 µL of a solution (concentration: 1 mg/mL) in acetonitrile of 2-[2-(pyrazole-1-yl)pyridine-5-yl]-6-tributylstannylimidazo[1,2-a]pyridine synthesized in Example 10, 170 µL of 1 mol/L hydrochloric acid, 60 µL of [$^{123}$I]sodium iodide of 426 MBq and 10 µL of 30% (w/v) hydrogen peroxide were added. After the mixed solution was left to stand at 40° C. for 10 minutes, it was subjected to HPLC under the following conditions, to obtain a fraction of [$^{123}$I]-6-iodo-2-[2-(pyrazole-1-yl)pyridine-5-yl]imidazo[1,2-a]pyridine.

HPLC Conditions:

Column: YMC PackPro C8 (trade name; manufactured by YMC; size: 4.6×150 mm)

Mobile phase: 0.1% trifluoroacetic acid-containing water/0.1% trifluoroacetic acid-containing acetonitrile=80/20 to 10/90 (20 minutes)

Flow rate: 1.0 mL/min.
Detector: Ultraviolet visible absorptiometer (Detection wavelength: 260 nm) and radioactivity counter (manufactured by raytest: type STEFFI)

10 mL of water was added to the fraction. The resulting solution was passed through Sep-Pak (registered trademark) C18 column (trade name: Sep-Pak (registered trademark) Light C18 Cartridges manufactured by Waters; the packed amount of the packing agent: 130 mg) so that the column adsorbed and collected [$^{123}$I]-6-iodo-2-[2-(pyrazole-1-yl)pyridine-5-yl]imidazo[1,2-a]pyridine. The column was rinsed with 1 mL of water, and then 1 mL of diethyl ether was passed therethrough, to elute [$^{123}$I]-6-iodo-2-[2-(pyrazole-1-yl)pyridine-5-yl]imidazo[1,2-a]pyridine. The obtained radioactivity was 49 MBq at the end of synthesis. Further, TLC analysis was conducted under the following conditions, and as a result, the radiochemical purity of the compound was 97.8%.

TLC Analysis Conditions:
TLC plate: Silica Gel 60 $F_{254}$ (trade name; manufactured by Merck & Co., Inc.)
Mobile phase: Ethyl acetate/methanol/diethylamine=100/4/1
Detector: Rita Star (trade name; manufactured by raytest)

Example 12

Measurement of Amyloid Binding Property

Binding properties to amyloid aggregates of Compound 1, Compound 3, Compound 4, Compound 5 and [$^{123}$I]-IMPY were evaluated by the following in vitro binding test.

The assay was conducted using a gray matter homogenate of brain of AD patients and a white matter homogenate of brain of AD patients, which were prepared from a brain tissue (Frontal lobe) of AD patients commercially available from Analytical Biological Services Inc. (United States). Meanwhile, it was confirmed that the brain tissue used in the present experiment showed amyloid deposition in the gray matter but showed no amyloid to be present in the white matter, by immunostaining with an anti-amyloid antibody {Anti-Human Amyloidβ(N) (82E1) Mouse IgG MoAb (Immuno-Biological Laboratories Co., Ltd.)} using thin slices derived from a common donor.

Method

A solution of Compound 1, Compound 3, Compound 4, Compound 5 or [$^{123}$I]-IMPY was adjusted to a radioactive concentration of 50 MBq/mL using a physiological saline solution containing 50 mmol/L of L-cysteine hydrochloride. The prepared solution was diluted with a 0.1% bovin serum albumin (hereinafter referred to as BSA)-containing 5 mmol/L phosphate buffer saline solution so that the respective test substances had a concentration of 0.05 to 5.5 pmol/L in the reaction solution, to obtain a sample solution. To each well of a 96-well microplate, 150 μL of a 0.1% BSA-containing 5 mmol/L phosphate buffer saline solution and 50 μL of a sample solution prepared above were added. Two wells were afforded to each sample solution. Of the two wells in which each sample solution was added, one received 50 μL of the brain grey matter homogenate of AD patients, and the other received 50 μL of the brain white matter homogenate of AD patients (final concentration: 100 μg protein/mL), so that the reaction was initiated. After the reaction solution was shaken for 3 hours (22° C., 400 rpm), a glass fiber filter (Multiscreen HTS FB, manufactured by Millipore) was used to filter the reaction solution. The filtrated filter was washed with a 0.1% BSA-containing 5 mmol/L phosphate buffer saline solution (200 μL, 3 times), and then radioactivity remained in the filter was measured with an Autowell Gammma system (type: ARC-7001, manufactured by Aloka). The ratio (%) of the radioactivity attached to the brain grey matter homogenate of AD patients or the brain white matter homogenate of AD patients relative to the added-radioactivity was calculated from the resulting count. Meanwhile, the above was repeated 3 times.

Results

Figure 6:
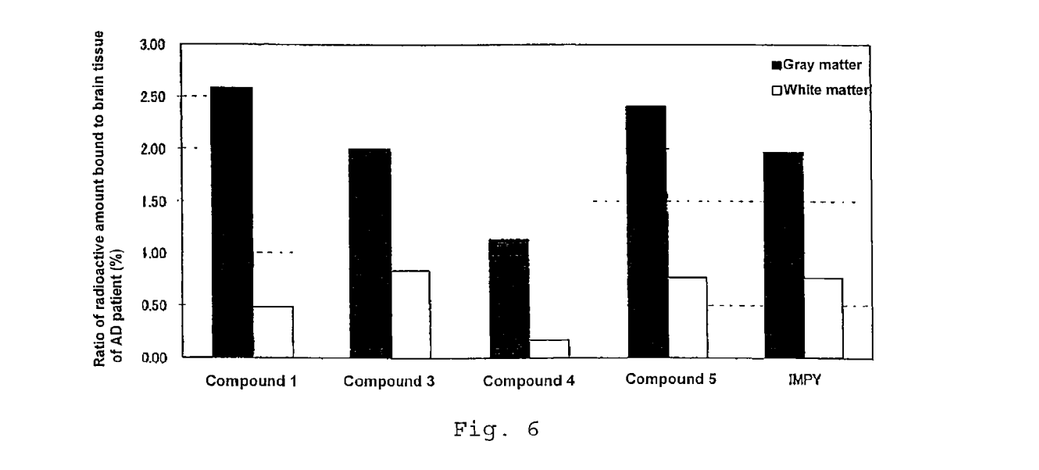
FIG. 6 is a ratio (%) of radioactivity attached to brain gray matter homogenate of AD patients or brain white matter homogenate of AD patients.
Figure 7:
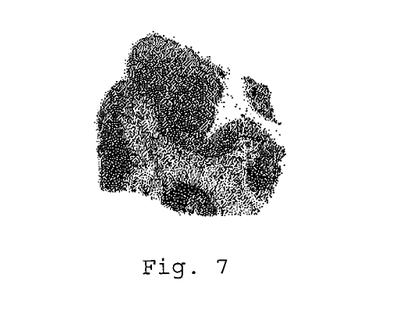
FIG. 7 is an autoradiography of a brain slice of an AD patient using [$^{123}$I]-6-iodo-2-[2-(1H-1,2,3-triazole-1-yl)pyridine-5-yl]imidazo[1,2-a]pyridine.
Figure 8:
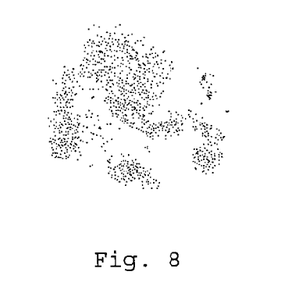
FIG. 8 is an autoradiography of a brain slice of an AD patient using [$^{123}$I]-6-iodo-2-[2-(2H-1,2,3-triazole-2-yl)pyridine-5-yl]imidazo[1,2-a]pyridine.
Figure 9:
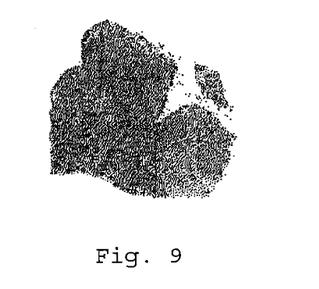
FIG. 9 is an autoradiography of a brain slice of an AD patient using [$^{123}$I]-6-iodo-2-[2-(1H-imidazole-1-yl)pyridine-5-yl]imidazo[1,2-a]pyridine.
Figure 10:
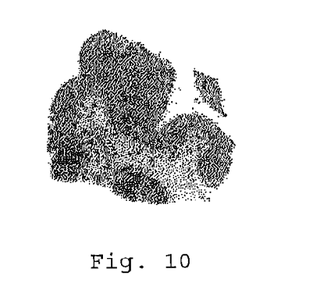
FIG. 10 is an autoradiography of a brain slice of an AD patient using [$^{123}$I]-6-iodo-2-[2-(1H-1,2,4-triazole-1-yl)pyridine-5-yl]imidazo[1,2-a]pyridine.
Figure 11:
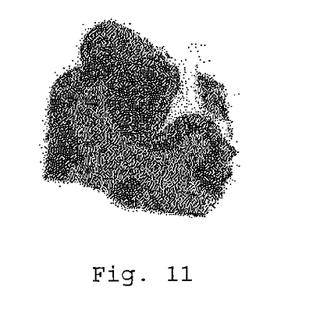
FIG. 11 is an autoradiography of a brain slice of an AD patient using [$^{123}$I]-6-iodo-2-[2-(pyrazole-1-yl)pyridine-5-yl]imidazo[1,2-a]pyridine.
Figure 12:
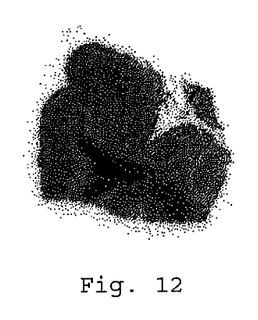
FIG. 12 is an autoradiography of a brain slice of an AD patient using [$^{123}$I]-IMPY.

The results are shown in FIG. 6 and Table 3. The group to which the brain grey matter homogenate of AD patients was added mostly showed high values of binding ratio (%) compared to the group to which the brain white matter homogenate of AD patients was added. Therefore, it was suggested that Compound 1, Compound 3, Compound 4 and Compound 5 have a binding property to amyloid deposited in the brain like $^{123}$I-IMPY.

TABLE 3

Ratio of radioactive amount attached to gray matter or white matter of brain of AD patients (%)

| Compound | Radioactive amount attached to brain tissue of AD patients (%) | |
|---|---|---|
| | Gray matter | White matter |
| Compound 1 | 2.59 | 0.48 |
| Compound 3 | 2.00 | 0.83 |
| Compound 4 | 1.13 | 0.17 |
| Compound 5 | 2.41 | 0.77 |
| [$^{123}$I]-IMPY | 1.97 | 0.77 |

Example 13

Measurement of Transferability into Brain and Clearance

Using Compound 1, Compound 2, Compound 3, Compound 4 and Compound 5, radioactive accumulation in brain of male Wistar rats (8-week old) was measured.

Method

A solution in which Compound 1, Compound 2, Compound 4 and Compound 5 were respectively dissolved in a physiological saline solution containing 50 mmol/L of L-cysteine hydrochloride was prepared, to obtain a sample solution (radioactive concentration: all 37 MBq/mL). A solution in which Compound 3 was dissolved in a physiological saline solution containing 10% ethanol and 50 mmol/L of L-cysteine hydrochloride was prepared, to obtain a sample solution (radioactive concentration: 37 MBq/mL). The sample solution was injected under non-anesthesia into the tail vein of male Wistar rats (8-week old) (dosage: 0.2 mL, dosed radioactivity: 7.4 MBq equivalent). The rats were sacrificed by decapitating under non-anesthesia to sample bloods and brains 2 and 60 minutes after the injection. Brains were subjected to measurement of mass of brains and further subjected to measurement of radioactivity (hereinafter referred to as A in this Example) with a single channel analyzer (detector type: SP-20 manufactured by OHYO KOKEN KOGYO Co., Ltd.). Further, the radioactivity level of the rest of the whole body including blood was measured in the same manner as above (hereinafter referred to as B in this Example). Using these measurement results, the amount of radioactive accumulation per unit weight of brain (% ID/g) at the respective time points after the dissection were calculated in accordance with the following formula (2).

Separately, a solution in which [$^{123}$I]-IMPY was dissolved in a physiological saline solution containing 50 mmol/L of L-cysteine hydrochloride (radioactive concentration: 37 MBq/mL) was prepared. The same procedure as the above was carried out to calculate the amount of radioactive accumulation per unit weight of brain (% ID/g) at the respective time points after the dissection.

Meanwhile, in this Example, three animals were used for the experiment at the respective time points.

$$\% \ ID/g = \frac{A}{B \times \text{brain weight}} \times 100 \qquad (2)$$

Results

The results are shown in Table 4. As shown in Table 4, Compounds 1, 2, 3, 4 and 5 showed a significant radioactive accumulation like $^{123}$I-IMPY at the time point of two minutes after the injection, and then showed a tendency to rapidly clear away in 60 minutes. These results suggest that Compounds 1, 2, 3, 4 and 5 possess excellent transferability to brain and rapid clearance from brain like $^{123}$I-IMPY.

TABLE 4

Radioactive accumulation in brain of the present compound after intravenous injection (rats)

| Compound | Radioactive accumulation per unit weight (% ID/g) | |
|---|---|---|
| | After 2 min. | After 60 min. |
| Compound 1 | 1.226 | 0.028 |
| Compound 2 | 1.160 | 0.027 |
| Compound 3 | 1.186 | 0.246 |
| Compound 4 | 1.287 | 0.056 |
| Compound 5 | 1.500 | 0.079 |
| [$^{123}$I]-IMPY | 1.644 | 0.085 |

Example 14

Confirmation of Compound Avidity for Brain Slice of AD Patients by Autoradiography The following experiment was carried out in order to examine whether the compound of the present invention can image amyloid in brain of AD patients.

Method (1) A 5 μm thick brain slice of AD patients was prepared from a brain tissue of AD patients available from Analytical Biological Services Inc. (United States).

(2) The brain slice prepared for each test substance was immersed in PBS 3 times in total: 15 minutes, 5 minutes and 5 minutes in this order. Next, it was immersed in a 1% BSA-containing PBS for 30 minutes to conduct hydrophilization. As the test substance, a 1% BSA-containing PBS containing each of Compound 1, Compound 2, Compound 3, Compound 4, Compound 5 and [$^{123}$I]-IMPY (radioactive concentration: 10 kBq/mL) was prepared and used. The above hydrophilized brain slice was immersed at room temperature in each of the test substance solutions. Then, it was immersed in a 1% BSA-containing PBS for 5 minutes, next in a PBS for 5 minutes and further in a PBS for 5 minutes to wash the brain slices. The washed brain slice was sufficiently dried, and then exposed to an imaging plate for 16 hours, and then autoradiogram image analysis was carried out by use of a Bio-imaging Analyzer (type: BAS-2500; manufactured by FUJIFILM Corporation) (FIG. 7, FIG. 8, FIG. 9, FIG. 10, FIG. 11, FIG. 12).

Figure 13:
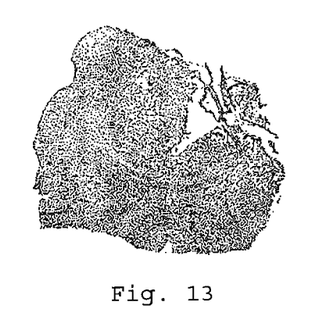
FIG. 13 is an immunostaining of a brain slice of an AD patient using anti-amyloid antibody.

(3) Separately, immunostaining at a site of amyloid deposition with an anti-amyloid antibody was carried out using adjacent slices which were subjected to hydrophilization in accordance with the same procedures as the above. Anti-Human Amyloidβ(N) (82E1) Mouse IgG MoAb (Immuno-Biological Laboratories Co., Ltd.) was used as the anti-amyloid antibody, and Anti-Mouse IgG (H+L) Goat IgG Fab'-HRP (Immuno-Biological Laboratories Co., Ltd.) was used as a secondary antibody. The site of amyloid deposition was detected by applying the DAB+(3,3'-diaminobenzidinetetrahydrochloride) substrate kit (Dako) to HRP attached to the secondary antibody (FIG. 13).

Results

FIG. 7, FIG. 8, FIG. 9, FIG. 10, FIG. 11 and FIG. 12 respectively show autoradiograms of the slices immersed in the solutions containing Compound 1, Compound 2, Compound 3, Compound 4, Compound 5 and [$^{123}$I]-IMPY, respectively. Amyloid deposition was confirmed by immunostaining at a gray matter site of the frozen brain slice of AD patients used in this experiment (FIG. 13), and the binding of the compounds to the site of amyloid deposition confirmed by immunostaining was also be confirmed on the respective autoradiograms. These results suggest that Compound 1, Compound 2, Compound 3, Compound 4 and Compound 5 according to the present invention can image the site of amyloid deposition in the brain like [$^{123}$I]-IMPY.

INDUSTRIAL APPLICABILITY

The compounds of the present invention can be utilized in the field of diagnostic agents.

The invention claimed is:

1. A compound represented by the following formula (1), or a salt thereof:

wherein $R^1$ is a radioactive iodine substituent, 0 to 2 of $A^1$, $A^2$, $A^3$ and $A^4$ represent N, and the rest thereof represent CH.

2. A compound or a salt thereof according to claim 1, wherein $R^1$ is selected from the group consisting of $^{123}$I, $^{124}$I, $^{125}$I and $^{131}$I.

3. A compound or a salt thereof according to claim 2, which is selected from the group consisting of [$^{123}$I]-6-iodo-2-[2-(1H-pyrrole-1-yl)pyridine-5-yl]imidazo[1,2-a]pyridine, [$^{123}$I]-6-iodo-2-[2-(pyrazole-1-yl)pyridine-5-yl]imidazo[1,2-a]pyridine, [$^{123}$I]-6-iodo-2-[2-(1H-imidazo-1-yl)pyridine-5-yl]imidazo[1,2-a]pyridine, [$^{123}$I]-6-iodo-2-[2-(1H-1,2,3-triazole-1-yl)pyridine-5-yl]imidazo[1,2-a]pyridine, [$^{123}$I]-6-iodo-2-[2-(1H-1,3,4-triazole-1-yl)pyridine-5-yl]imidazo[1,2-a]pyridine, [$^{123}$I]-6-iodo-2-[2-(2H-1,2,3-triazole-2-yl)pyridine-5-yl]imidazo[1,2-a]pyridine and [$^{123}$I]-6-iodo-2-[2-(1H-1,2,4-triazole-1-yl)pyridine-5-yl]imidazo[1,2-a]pyridine.

4. A compound represented by the following formula (2), or a salt thereof:

wherein R² is a group selected from the group consisting of a non-radioactive halogen substituent, nitro group, trialkylammonium group having alkyl chains with 1 to 4 carbon atoms, trialkylstannyl substituent having alkyl chains with 1 to 4 carbon atoms and triphenylstannyl group, 0 to 2 of $A^5$, $A^6$, $A^7$ and $A^8$ represent N, and the rest thereof represent CH.

5. A diagnostic agent for Alzheimer's disease, which comprises a compound represented by the following formula (1), or a salt thereof:

wherein $R^1$ is a radioactive iodine substituent, 0 to 2 of $A^1$, $A^2$, $A^3$ and $A^4$ represent N, and the rest thereof represent CH.

6. The diagnostic agent for Alzheimer's disease according to claim 5, wherein $R^1$ is selected from the group consisting of $^{123}I$, $^{124}I$, $^{125}I$ and $^{131}I$.

7. The diagnostic agent for Alzheimer's disease according to claim 6, which comprises a compound selected from the group consisting of [$^{123}I$]-6-iodo-2-[2-(1H-pyrrole-1-yl)pyridine-5-yl]imidazo[1,2-a]pyridine, [$^{123}I$]-6-iodo-2-[2-(pyrazole-1-yl)pyridine-5-yl]imidazo[1,2-a]pyridine, [$^{123}I$]-6-iodo-2-[2-(1H-imidazole-1-yl)pyridine-5-yl]imidazo[1,2-a]pyridine, [$^{123}I$]-6-iodo-2-[2-(1H-1,2,3-triazole-1-yl)pyridine-5-yl]imidazo[1,2-a]pyridine, [$^{123}I$]-6-iodo-2-[2-(1H-1,3,4-triazole-1-yl)pyridine-5-yl]imidazo[1,2-a]pyridine, [$^{123}I$]-6-iodo-2-[2-(2H-1,2,3-triazole-2-yl)pyridine-5-yl]imidazo[1,2-a]pyridine and [$^{123}I$]-6-iodo-2-[2-(1H-1,2,4-triazole-1-yl)pyridine-5-yl]imidazo[1,2-a]pyridine, or salt thereof.

\* \* \* \* \*